(12) United States Patent
Chen et al.

(10) Patent No.: US 10,376,715 B2
(45) Date of Patent: Aug. 13, 2019

(54) SYSTEM AND METHOD FOR THE VALIDATION AND QUALITY ASSURANCE OF COMPUTERIZED CONTOURS OF HUMAN ANATOMY

(71) Applicant: Washington University, St. Louis, MO (US)

(72) Inventors: Hsin-Chen Chen, Clayton, MO (US); Sasa Mutic, Creve Coeur, MO (US); Jun Tan, Coppell, TX (US); Michael Altman, University City, MO (US); James Kavanaugh, University City, MO (US); Hua Li, Chesterfield, MO (US)

(73) Assignee: Washington University, St. Louis, MO (US)

( * ) Notice: Subject to any disclaimer, the term of this patent is extended or adjusted under 35 U.S.C. 154(b) by 677 days.

(21) Appl. No.: 14/700,592

(22) Filed: Apr. 30, 2015

(65) Prior Publication Data
US 2015/0297916 A1 Oct. 22, 2015

Related U.S. Application Data

(63) Continuation-in-part of application No. 14/454,000, filed on Aug. 7, 2014, now Pat. No. 9,626,757.
(Continued)

(51) Int. Cl.
*A61N 5/10* (2006.01)
*G06T 7/13* (2017.01)

(52) U.S. Cl.
CPC .............. *A61N 5/1039* (2013.01); *G06T 7/13* (2017.01); *G06T 2207/10081* (2013.01);
(Continued)

(58) Field of Classification Search
CPC ................... A61N 5/1039; G06T 7/13; G06T 2207/20081; G06T 2207/30004; G06T 2207/10081; G06T 2207/10116
See application file for complete search history.

(56) References Cited

U.S. PATENT DOCUMENTS 7,194,122 B2  3/2007 Faber et al.
7,369,694 B2  5/2008 Barfuss et al.
(Continued)

*Primary Examiner* — Kaylee R Wilson
(74) *Attorney, Agent, or Firm* — Armstrong Teasdale LLP

(57) ABSTRACT

A system and method for validating the accuracy of delineated contours in computerized imaging using statistical data for generating assessment criterion that define acceptable tolerances for delineated contours, with the statistical data being conditionally updated and/or refined between individual processes for validating delineated contours to thereby adjust the tolerances defined by the assessment criterion in the stored statistical data, such that the stored statistical data is more closely representative of a target population. In an alternative embodiment, a system and method for validating the accuracy of delineated contours in computerized imaging using machine learning for assessing delineated contours, with the machine learning training data being used to generate geometric attributes, and the geometric attributes used to construct intra- and interstructural geometric attribute distribution models to automatically detect contouring errors. The present invention may be used to facilitate, as one example, radiation therapy.

10 Claims, 15 Drawing Sheets

Related U.S. Application Data

(60) Provisional application No. 61/863,677, filed on Aug. 8, 2013.

(52) U.S. Cl.
CPC ............... *G06T 2207/10116* (2013.01); *G06T 2207/20081* (2013.01); *G06T 2207/30004* (2013.01)

(56) References Cited

U.S. PATENT DOCUMENTS

| | | |
|---|---|---|
| 7,474,776 B2 | 1/2009 | Kaufman et al. |
| 7,742,629 B2 | 6/2010 | Zarkh et al. |
| 8,019,042 B2 | 9/2011 | Shukla et al. |
| 8,081,813 B2 | 12/2011 | Nelms et al. |
| 8,218,905 B2 | 7/2012 | Dekel et al. |
| 8,249,345 B2 | 8/2012 | Wu et al. |
| 8,526,700 B2 | 9/2013 | Isaacs |
| 8,705,828 B2 | 4/2014 | Yang et al. |
| 2017/0091574 A1 * | 3/2017 | Udupa .................. G06K 9/4638 |

\* cited by examiner

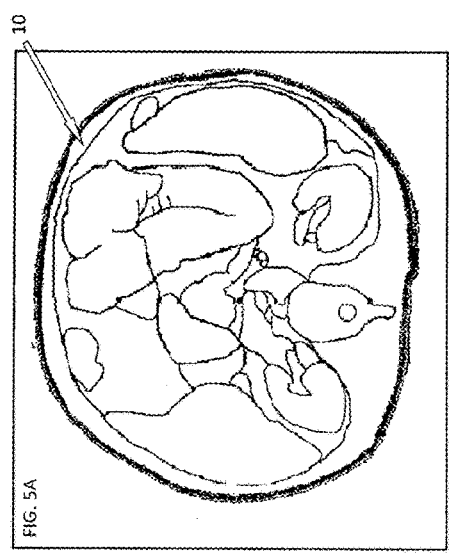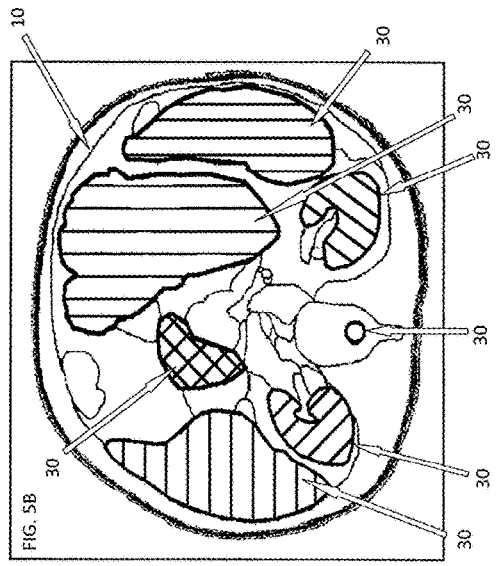
FIG. 5A
FIG. 5B

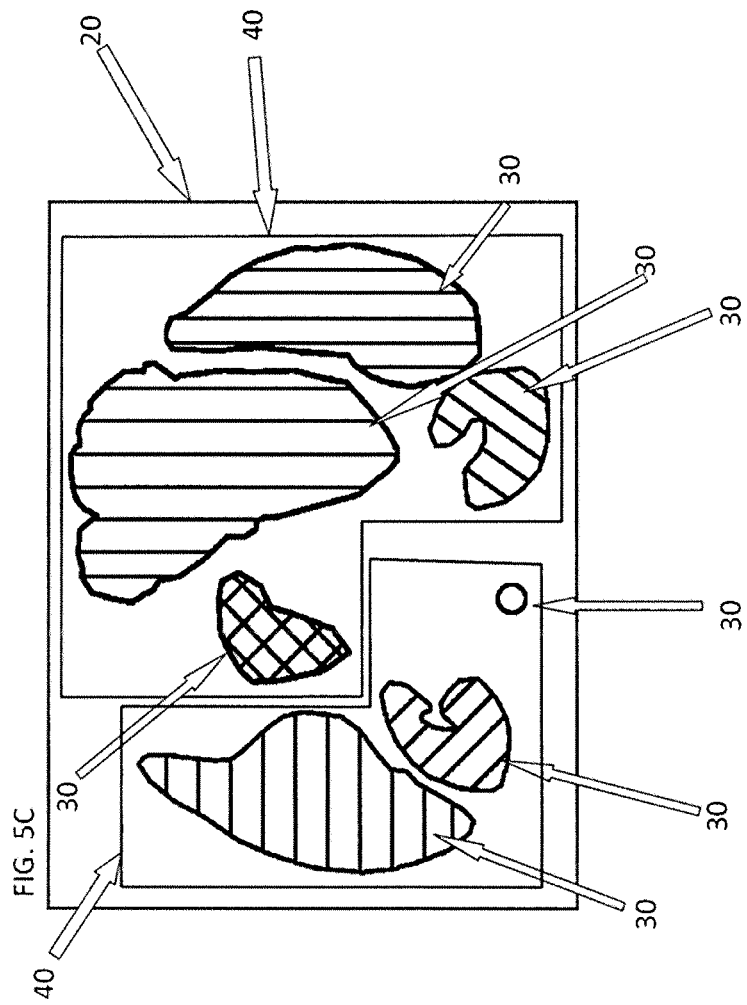

SYSTEM AND METHOD FOR THE VALIDATION AND QUALITY ASSURANCE OF COMPUTERIZED CONTOURS OF HUMAN ANATOMY

CROSS-REFERENCE TO RELATED APPLICATION

This application claims priority as a continuation-in-part application from U.S. patent application Ser. No. 14/454,000 filed on Aug. 7, 2014, which claims priority to U.S. Provisional Patent Application Ser. No. 61/863,677, filed Aug. 8, 2013, both of which are incorporated herein in their entirety.

FIELD OF THE INVENTION

The present invention relates to automated quality control of computerized representations of human anatomy and methods of performing such quality control. In particular, the present invention relates to an apparatus and method for assessing the validity and quality of delineated anatomies in computerized patient imaging. The present invention may be used to facilitate, as one example, on-line adaptive radiation therapy.

BACKGROUND OF THE INVENTION

The use of digital imaging of human anatomy, for medical or other purposes, is ubiquitous and comes in many forms and methods of acquisition. Digital imaging encompasses the conversion ("digitization") of analog imaging media into digital representations, such as scanning a physical x-ray film, as well as the use of digital detectors on devices such as computed tomography machines, magnetic resonance imagers, and positron emission tomography. In the latter cases, the imaging data exists only digitally. The wide use of computer-based imaging and display systems has been spurred by enhancements in speed, reduction in terms of cost of materials and storage space, as well as ease of transfer, storage, and display, among other factors.

While digital imaging provides computerized representations of a patient's anatomy, the delineation of individual structures ("delineated anatomy" or "contours" of structures such as tissues, organs, and etc.) within those images can be important for diagnostic and/or therapeutic purposes. In clinical practice, this delineation (also called "contouring") of a patient's anatomy is performed with user-driven, computer-based tools and/or computer-vision-based automated techniques ("auto-contouring").

Delineated anatomy can serve a number of useful purposes. In radiology, for example, delineated anatomy can be used to aid in the detection of tumors from screening images. In radiation oncology, the delineated anatomy can be used to guide and optimize the planning of cancer treatment, where spatially targeted dosages of ionizing radiation are applied to a tumor or other region containing cancerous or malignant tissue. Growing and rapidly multiplying cancer cells tend to be more susceptible to damage from ionizing radiation as compared with normal cells, and higher dosage administrated by properly planning the applied radiation can preferentially destroy cancerous or malignant tissue. However, ionizing radiation is harmful to both malignant and healthy cells, and so precise spatial targeting of the radiation is important for applying effective radiation therapy to the malignancy while limiting collateral damage to healthy tissue. Typically during a procedure, one or more beams are directed at a tumor. Angular coverage can be achieved by using a plurality of stationary radiation sources distributed around the subject, or by revolving a single radiation source, such as a linear accelerator, around the subject (i.e., tomotherapy). These beams must be controlled such that the targeted tumor receives enough radiation so as to at least partially destroy it, while minimizing the amount of damage to surrounding non-tumorous tissue. In addition, the use of multiple beams from several angles increases the need for accurate contouring, as it is imperative that the shape and intensity be tailored to keep the integrated exposure of certain radiation-sensitive critical organs below a safety threshold.

Radiation therapy is planned in advance for a specific subject based on imaging data acquired for that subject and the resulting structure contours generated on these images. As such, organ-at-risk (OAR) and tumor contouring is a critical step in radiation therapy treatment process.

While both manual and automated approaches to contouring exist, current approaches are prone to errors due to the large degree of inter- and intraobserver variability. These errors can arise from the limitations of medical imaging technology in terms of visualizing human anatomy, which may have insufficient contrast, resolution, or both. Also contributing to errors is the inherent anatomical variability among individuals. Physicians and/or other clinicians often must evaluate and reverify all radiation therapy contours before their use. In current practices, this requires one or more users to conduct a manual evaluation to assess the accuracy of the delineated anatomy and ensure proper surface contouring and labeling. This manual evaluation is both time consuming and relies on user expertise, alertness, and other human factors to identify potential errors in the delineated anatomy. Failure to detect errors in delineated anatomy can lead to complications ranging from negligible to catastrophic within medical procedures that rely on this data. As such, evaluation of the anatomy delineation accuracy is a mandatory and very important step in all cases.

While it is recognized that evaluating a given contouring for quality assurance purposes is an important step in radiation therapy treatment, there remains substantial impediments to reliably automating the process. Previously developed solutions have included atlas-based systems, where population-based "standard" atlas of structures are used as a benchmark. The atlas-based systems typically use Dice coefficients or other similarities indices for validation, generally against some defined landmarks (i.e., a set of points, frequently user-determined). The atlas-based approaches have several deficiencies. First, the variation from person to person in anatomical structures makes using an atlas-based approach difficult. Furthermore, there are a number of different variations in anatomical structures between populations of persons (based, for example, on sex, height, weight, ethnicity, socioeconomic status, medical history, among many other factors). As such, these methods generally result in some broad dataset (one "man" or "woman", for example), which results in limited overall utility. Also, atlases, once created, tend to remain fixed in terms of what they contain. Thus analyzing an object or structure not contained within the atlas is not an option for an end-user. Finally, an atlas' reliance on landmark-based similarity coefficients may limit the accuracy of the evaluation to locations near the points of interest. The accuracy of employing point-based similarity coefficients is, as a result, largely dependent on the number of points/landmarks used.

Another previously developed approach to evaluating contouring has been the use of patient-specific "gold standard" dataset. This approach also suffers from a number of limitations. Particularly, a gold standard approach requires that some set of delineated anatomy determined for a given person be designated as the "true" set of structures for that person. This can be done, for example, by assuming that the first set of a series of delineated anatomical structures for a patient is the "truth," such as the first of a time series of images acquired throughout therapy to determine how one or more structures of interest change shape, size, and/or position. Such "gold-standard" algorithms are limited by the fact that the "truth" dataset must itself be validated manually and is thus prone to errors that would then be propagated through all subsequently analyzed images. Point-based similarity indices are also frequently used with these algorithms, carrying with that the limitations as noted above.

There is, therefore, a need in the art for decreasing the time required for evaluating the accuracy of delineated anatomies as well as for increasing the robustness and reliability of these evaluations in identifying any errors in the evaluated delineated anatomy. At the same time, there is a need in the art for an evaluation system that provides those benefits while also allowing for flexibility and customizability to evaluate an array of image modalities, populations of persons, and/or anatomical structures of interest.

SUMMARY OF THE INVENTION

The present invention is directed at a device for automated quality control of computerized representations of human anatomy; and methods of performing such quality control.

The present invention concerns a delineated contour validation process, and a system for delineated contour validation, for validating the accuracy of delineated contours in computerized imaging. The method includes judging the accuracy of a delineated contour using stored statistical data defining clinically acceptable tolerances for one or more delineated contours. The stored statistical data is conditionally updated and/or refined by resultant data generated from individual performances of the delineated contour validation process, such that over subsequent performances of the delineated contour validation process, the stored statistical data may be made to define clinically acceptable tolerances that account for variances in a targeted population.

The system includes, among other components, a storage unit storing statistical data defining clinically acceptable tolerances for one or more delineated contours; and a processor configured to conditionally update and/or refine the stored statistical data by the resultant data generated from individual operations of the delineated contour validation system.

In further detail, the method and system of the present invention are both inclusive of steps and structural components for validating delineated contours. In an exemplary delineated contour validating process, the process will begin by accessing a data set that includes one or more computer representations of a patient's anatomy, with the one or more computer representations including one or more delineated anatomies; then accessing a storage unit storing one or more assessment metrics for use in analyzing delineated anatomies in computer representations, and selecting one or more assessment metrics for use in analyzing the delineated anatomies in the computer representations of the accessed data set; and then applying the selected assessment metrics to the delineated anatomies in the computer representations of the accessed data set to generate one or more resultant metrics.

In another step, access is made of a storage unit storing statistical data that comprises one or more metric standards and one or more metric modifiers to generate one or more assessment criterion that define acceptable tolerances for resultant metrics generated from application of corresponding assessment metrics to a delineated anatomy. A selection is made of one or more metric standards and, optionally, one or more metric modifiers to generate one or more assessment criterion that correspond to earlier selected one or more assessment metrics, for use in judging one or more resultant metrics generated from applying the earlier selected one or more assessment metrics to a delineated anatomy.

A judgment is made of the one or more generated resultant metrics by comparing each generated resultant metric against a corresponding one of the generated assessment criterion to determine if each generated resultant metric satisfies the tolerances defined by the corresponding assessment criterion.

A storage unit is accessed to store, at least temporarily, the judgment results from judging the generated resultant metrics against the generated assessment criterion. A positive result is recorded for each resultant metric that is judged to satisfy the tolerances defined by the corresponding assessment criterion, and a negative result is recorded for each resultant metric that is judged to not satisfy the tolerances defined by the corresponding assessment criterion. The stored judgment results are then accessed and a report is generated listing at least all negative stored results.

In an optional step, the one or more generated resultant metrics are conditionally recorded to the storage unit storing the statistical data comprising the metric standards and the metric modifiers. If the one or more generated resultant metrics are stored to the storage unit storing the statistical data, the statistical data is updated and/or refined to thereby adjust one or both of the metric standards and the metric modifiers, such that subsequent delineated contour validations may be performed using updated and/or refined assessment criteria that define clinically acceptable tolerances that account for variances in a targeted population.

The delineated contour validation process is capable of being performed, and the delineated contour validation system is capable of being operated in the performance of the method, to validate the accuracy of delineated contours without requiring a user to perform a manual evaluation of the contouring and/or labeling of the delineated contour itself In an alternate embodiment present invention concerns a delineated contour validation process, and a system for delineated contour validation, for validating the accuracy of delineated contours in computerized imaging. In one aspect, the method includes judging the accuracy of a delineated contour using machine learning, where the contouring framework uses approved radiation therapy contours as the training data set for a machine learning system such that inter- and intrastructural Geometric Attribute Distribution (GAD) models can be constructed, and patient specific contours can be fit to the models.

In accordance with one aspect of the invention, the system includes, among other components, a storage unit storing data defining clinically approved contours; and a processor configured to calculate geometric attributes, intra- and interstructural GAD models, and the errors in the contours. In one aspect, the system can also store additional contours, including the contour under evaluation, after having errors detected by the system.

In accordance with another aspect of the invention, contouring to define contours delineating a radiation target region and one or more risk regions in a planning image is performed. During the evaluation of the contouring, a 3D image of the contours, displaying the contouring errors, is produced.

In further detail of another aspect of the invention, the method and system of the present invention are both inclusive of steps and structural components for validating delineated contours. In an exemplary delineated contour evaluation process, the process will begin by accessing a data set that includes one or more computer representations of a patient's anatomy, with the one or more computer representations including one or more delineated anatomies; then calculating a geometric attribute based on the one or more computer representations. Further, the process constructs intra- and inter-structural GAD models.

In another another aspect of the invention, a patient specific delineated contour is accessed, and from this delineated contour, a geometric attribute is calculated. Using the patient specific geometric attribute and the intra- and inter-structural GAD model, the contouring errors can be detected.

In yet another aspect of the invention, a storage unit is accessed to store, at least temporarily, the resulting contouring errors. From the detected contouring errors, a contouring report can be generated. A physician can use the contouring error report in order to verify the patient specific contours. If the physician approves of the contouring, radiation therapy can be planned and treatment using the patient specific contour.

Both the foregoing general description and the following detailed description are exemplary and explanatory only, and are intended to provide further explanation of the invention as claimed. The accompanying drawings are included to provide a further understanding of the invention; are incorporated in and constitute part of this specification; illustrate several embodiments of the invention; and, together with the description, serve to explain the principles of the invention.

BRIEF DESCRIPTION OF THE DRAWINGS

Further features and advantages of the invention can be ascertained from the following detailed description that is provided in connection with the drawings described below:

FIGS. 5A-5C illustrate an exemplary computerized representation undergoing analysis according to the present invention.

DETAILED DESCRIPTION OF THE INVENTION

The following disclosure discusses the present invention with reference to the examples shown in the accompanying drawings, and illustrates examples of the invention though does not limit the invention to those examples.

The present invention relates to automated quality control of computerized representations of human anatomy and methods of performing such quality control. In particular, the present invention relates to an apparatus and method for assessing the validity and quality of delineated anatomies in computerized patient imaging. The system and method of use are discussed in greater detail below.

The Contour Validating System

Figure 2:
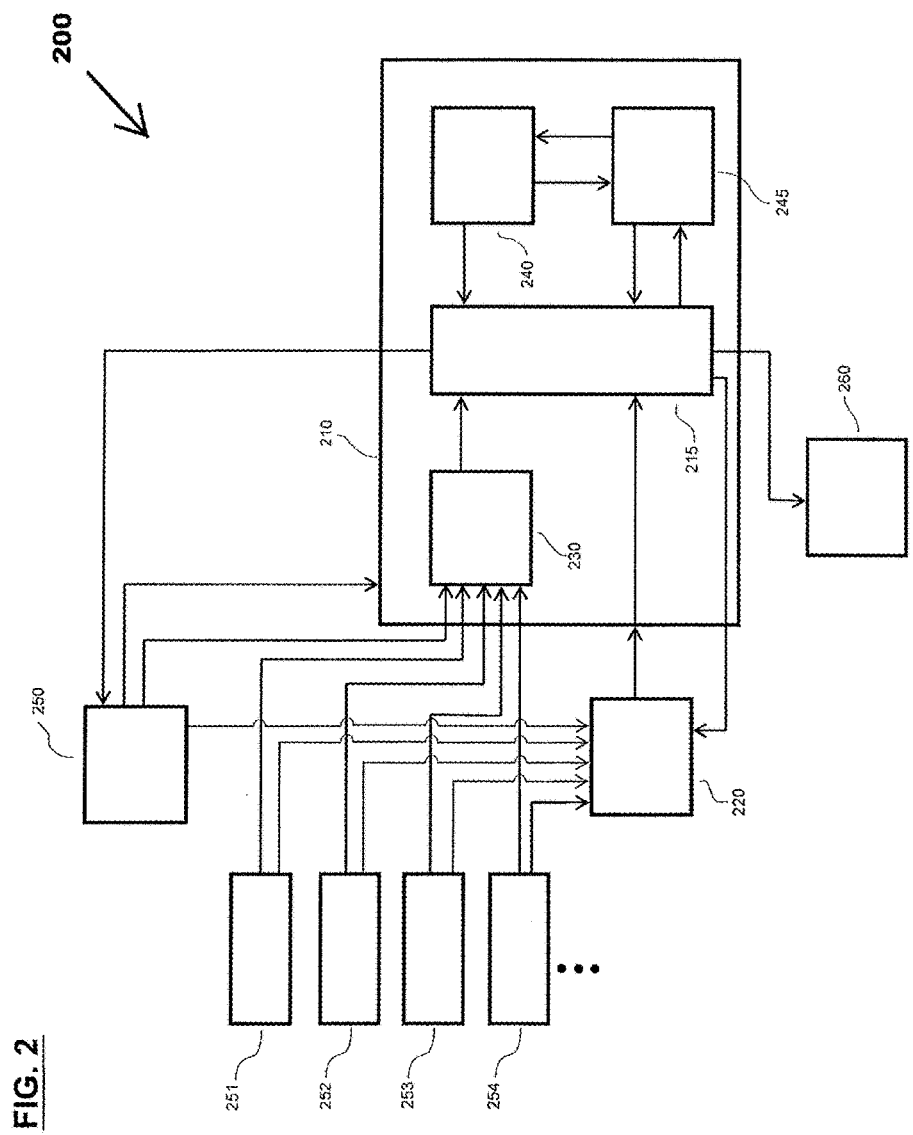
FIG. 2 illustrates a system for use in performing the process of FIG. 1.

FIG. 2 illustrates a system 200 for use in performing the processes 100 and 300. The system 200 includes a processor 210 for receiving input data, either in the form of a completely compiled data set, or in the form of individual data packets, which may subsequently be compiled into a data set. The processor 210 may include an internal compiler 230, a comparator 215, a permanent memory 240, and a temporary memory 245.

An input device 250 (e.g., a graphical user interface) is connected to the processor 210, and configured for a user to control the processor 210 and for a user to selectively enter data into the processor 210. A user may employ the input device 250 to control the processor 210 in executing the process 300. The user's control over the process 300 may include the selection of case-specific assessment metrics. In addition, a user may employ the input device 250 to enter information to the internal compiler for use in compiling a case-specific data set (e.g., information types such as patient-specific demographic and socioeconomic data). A user's entry of information to the internal compiler 230 may be dependent entirely on user discretion, or it may be responsive to automated queries generated at the input device 250 by the system 200. In some examples, the system may also communicate with an output device 260 (e.g., a printer) for reproducing information that is displayed to a user through the input device 250. Both the input device 250 and the output device 260 may be a part of the system 200 (e.g., a localized input device with the system), or one or both may be external to the system and connected over a network.

One or more additional input devices 251-254 may also be connected to the processor 210. The additional input devices 251-254 may each provide a specific information type to the compiler 230. For example, an input device 251 may provide patient-specific medical history from a geographically remote medical facility; while an input device 252 may provide patient-specific computerized representations (e.g., computerized images) of the patient's anatomy from a separate system in a common facility (e.g., input device 252 may be a CT scanning device in a separate department of a hospital where the system 200 is located). Additional input devices 253, 254, etc. may communicate with the processor 210 to provide additional information for compiling a data set (e.g., demographic data; socioeconomic data; etc.). Each of the input devices 251-254, etc., may be either geographically remote from the system 200, or locally-remote (e.g., inter-departmental within a common facility); and each communicating with the system 200 over a network.

The internal compiler 230 is configured to receive data from the input device 250 and to compile that information into a data set for use by the processor 210. In examples where one or more additional input devices 251-254, etc., are present, the internal compiler 230 is further configured to receive information from those additional input devices and to include that information in the compiled data set. The internal compiler 230 is also configured to parse data from the compiled data set in order to identify specific information types. For example, the internal compiler 230 may be configured to identify: one or more computerized representations; one or more delineated anatomies; one or more anatomical structures; the imaging modality for computerized representations 10; demographic data; socioeconomic status data; medical history data; and any other specific information type included in the data set. The internal compiler 230 communicates with the comparator 215 for transmitting specific information types for comparison with statistical data stored in one or both of the permanent memory 240 and the temporary memory 245.

An external compiler 220 may also be connected to the processor 210. An external compiler 220 may operate in similar fashion to the internal compiler 230; however, an external compiler 220 will enable the collection of information, and the compiling of a data set, at an external location from the system 200. For example, where multiple systems 200 are installed at different geographic locations, an external compiler 220 may be used to permit the individual systems 200 to access a common data collection. In some examples, each system 200 will be configured to not only receive data sets from a compiler 220, but also to send resultant metrics to the compiler 220 for updating the data collection stored in the compiler 220. As with the internal compiler 230, the external compiler likewise communicates with the comparator 215 for transmitting specific information types for comparison with statistical data stored in one or both of the permanent memory 240 and the temporary memory 245.

The permanent memory 240 stores statistical data for use in judging the accuracy of computerized representations of a patient's anatomy. In particular, the statistical data stored in the permanent memory unit 240 may include, though is not limited to: assessment metrics; metric standards; and metric modifiers. The permanent memory unit 240 may communicate with the comparator 215 either directly or through the temporary memory unit 245. The temporary memory unit 245 may be used to temporarily store: case-specific assessment metrics for use in analyzing a computerized representation of a patient's anatomy; case-specific resultant metrics generated from analyzing a computerized representation of a patient's anatomy; case-specific metric standards, and case-specific metric modifiers for generating case-specific assessment criteria; the generated assessment criteria for judging resultant metrics; and the judgment results from judging resultant metrics relative to assessment criteria. In some examples, the temporary memory unit 245 is capable of not only receiving data from the permanent memory unit 240, but also transferring data to the permanent memory unit 240 to thereby update and refine the statistical data stored therein. Although the example in FIG. 2 shows both memory units 240 and 245 locally arranged within the processor 210, one or both of the memory units 240 and 245 may alternatively be external to one or both of the processor 210 and the system 200.

The Contour Validating Method

Figure 1:
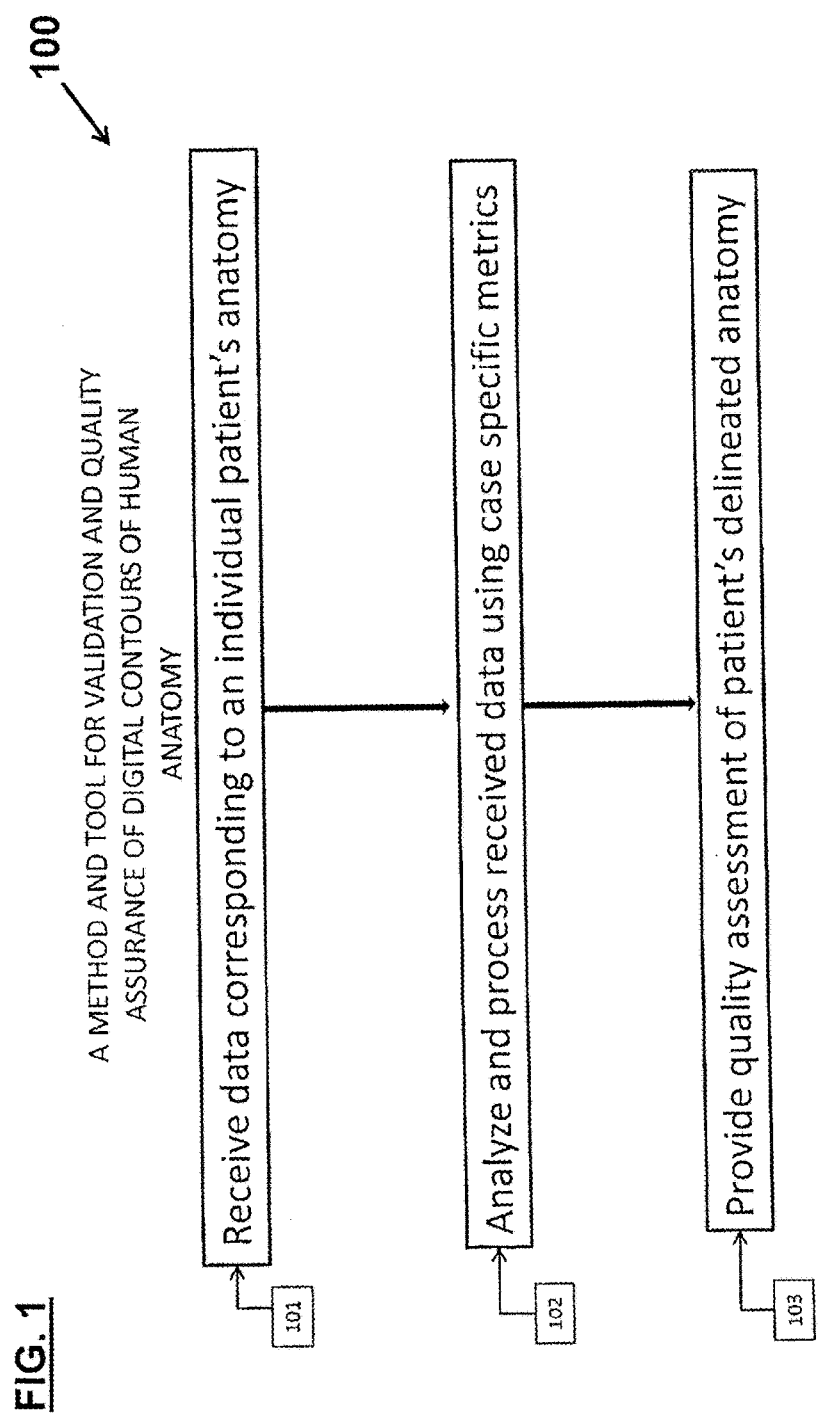
FIG. 1 illustrates a generalized process 100 for automated quality control of computerized representations of human anatomy.

FIG. 1 illustrates a general process 100 for assessing the delineation accuracy of one or more delineated anatomies in a computerized representation of a patient's anatomy. Hereafter the term "step" is abbreviated as "s", such that the phrase "step 101" is abbreviated as "s101". In s101, a data set having information specific to a patient is received at the processor 210. In s102, the received data set is parsed, and delineated anatomical structure sets 20 in the data set are identified. Also in s102, the individual delineated anatomical structure sets 20 are analyzed using a series of selected assessment metrics to generate a series of case-specific resultant metrics. In s103, an accuracy assessment is made of the delineated anatomies by judging the resultant metrics from s102 relative to corresponding assessment criteria; and a report detailing the accuracy assessment is generated and output for user review.

FIGS. 5A-5C show examples of computerized representations 10 of a patient's anatomy, with delineated anatomical structures 30 identified within delineated anatomical structure sets 20. In FIG. 5C, there is shown an example as to how delineated anatomical structures 30 might be grouped into two different delineated anatomical structure groupings 40.

Although the example in FIGS. 5A-5C shows a computerized representation 10 having a single delineated anatomical structure set 20, it is noted that a computerized representation 10 may instead have two or more delineated anatomical structure sets 20. Likewise, although the example in FIG. 5C shows a delineated anatomical structure set 20 that has two groupings 40, a computerized representation 10 may have only one grouping 40, or it may have three or more groupings 40. Also, one or more groupings 40 may overlap with one another by encompassing one or more common delineated anatomical structures 30. Furthermore, although the examples in FIGS. 5B and 5C both show seven examples of delineated anatomical structures 30, the computerized representations 10 may also have one to six, or eight or more delineated anatomical structures 30.

Figure 3:
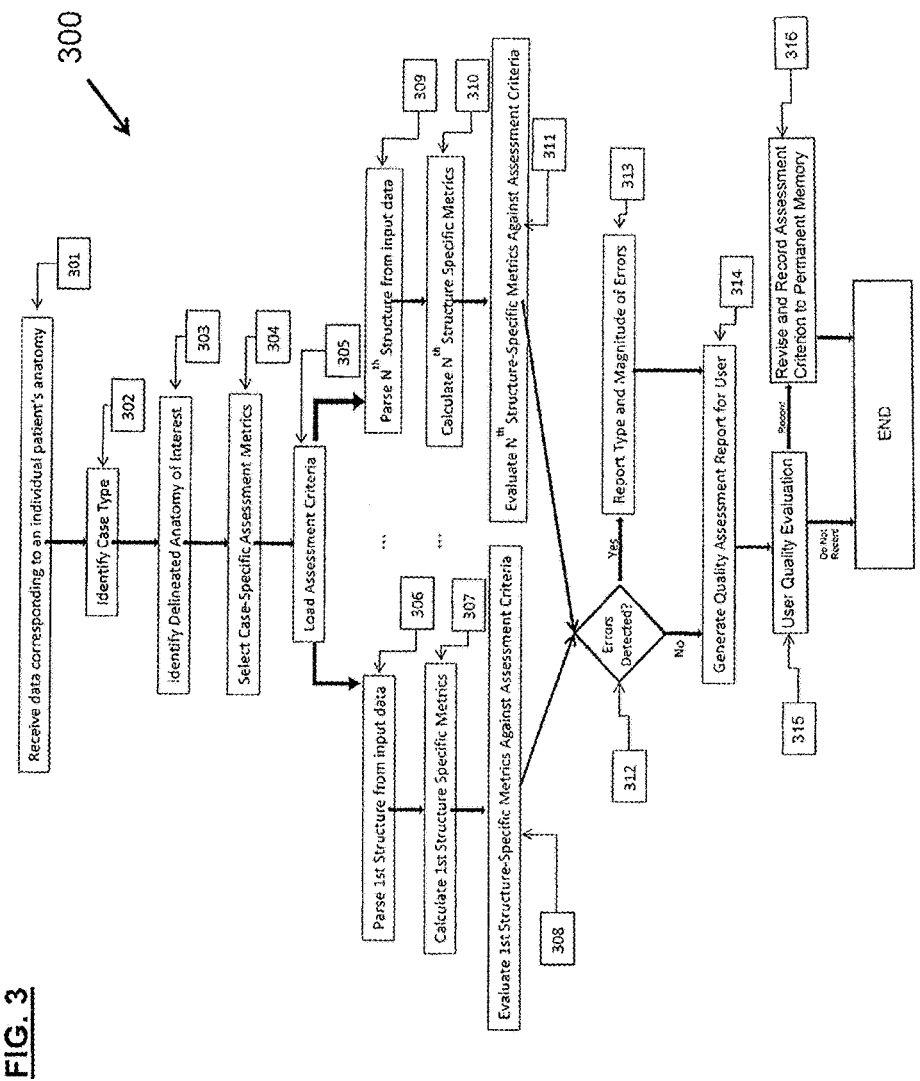
FIG. 3 illustrates further detailed steps for the process of FIG. 1.

FIG. 3 illustrates a further detailed process 300 for assessing the delineation accuracy of one or more delineated anatomical structure sets 20 in a computerized representation 10 of a patient's anatomy, such as those shown in FIGS. 5A-5C.

In s301, a data set is received at the processor 210. The received data set may include, though is not limited to: [i] one or more computerized representations 10 of a patient's anatomy (e.g., digitized images; analog recordings; and etc.); [ii] an anatomical designation (e.g., a designation of the delineated anatomical structure sets 20, delineated anatomical structures 30, and/or delineated anatomical groupings 40 that were targeted for imaging in the one or more computerized representations 10); [iii] a designation of the imaging modality for the computerized representations 10 (e.g., CT scans (helical; fan-beam; cone-beam; 4D; slow; and etc.); MR scans (T1 weighted; T2 weighted; proton density weighted; diffusion weighted; with or without contrast; and etc.); PET scans; SPECT scans; digital radiographs; digital subtraction radiographs; digitized analog radiographic images (such as films); and etc.); [iv] the patient's demographics (e.g., age; weight; height; gender; ethnicity; and etc.); [v] the patient's socioeconomic status (e.g., income; education; occupation; and etc.); [vi] information from the patient's medical history (e.g., physiological and/or anatomical irregularities; past morbidities; comorbidities; the situs of past and/or present morbidities which might influence an anatomy's geometry (e.g., locations of past and/or present infections, trauma, and the like which might influence size, shape, volume, etc. of an anatomy); pregnancy status; lifecycle status (pre-/post-menopausal, pre-/post-pubescent, and etc.); patient/disease genetics and/or presence of biomarkers; site and stage of current disease; presence of medical implants (pacemakers; pain pumps; joint; hip; or bone prostheses; tracheotomy tubes; and etc.); and the like) and [vii] factors relating to patient lifestyle (e.g. diet; frequency of exercise; sexual activity; smoking status and/or date of cessation; use of medications and/or recreational drugs, and etc.).

The various information making-up the data set may be collected and precompiled into the data set in advance by an external compiler 220, prior to receipt as a completed data set at the processor 210. Alternatively, the information making-up the data set may be received in piecemeal at the processor 210 (in two or more separate data packets), and compiled into the data set at the processor 210 by an internal compiler 230. The system 200 may be configured to receive data sets in both precompiled formats and piecemeal formats, such that a data set may be received selectively in either format as needed on a case-by-case basis.

In s302, the received data set is analyzed and designated with a case-type. Particularly, the system 200 will designate a received data set with a case-type by identifying certain information contained within the received data set as corresponding to one or more predetermined information types, and then selecting a case-type that specifies the information types identified within the received data set.

For example, a system 200 may be configured to identify each of the following predetermined information types: [i] one or more computerized representations of a patient's anatomy; [ii] an anatomical designation; [iii] a designation of the imaging modality for the computerized representations; [iv] the patient's demographics; [v] the patient's socioeconomic status; [vi] information from the patient's medical history; and [vii] patient lifestyle factors. With such a configuration, a system 200 will search a received data set to determine if the data set contains any information corresponding to any of the predetermined information types, such as the exemplary information types [i]-[vii]. Once the system 200 has searched the received data set and determined if the data set contains any information corresponding to any of the predetermined information types, the system 200 will then designate the received data set with a case-type indicating which of the predetermined information types is deemed present within the data set.

Thus, continuing with the foregoing example, if a received data set contains data corresponding to each of the exemplary predetermined information types [i]-[vii], then the data set will be designated with a case-type indicating that there is data present for all of the predetermined information types [i]-[vii]. Alternatively, if a received data set contains data corresponding to the exemplary predetermined information types [i], [iii], [v], and [vii], but is deemed to lack data corresponding to the exemplary predetermined information types [ii], [iv], and [vi] then the data set will be designated with a case-type indicating that there is data present only for the predetermined information types [i], [iii], [v], and [vii].

The designation of a case-type for a received data set may be done manually by a user reviewing the received data set (either externally of the system 200 or through a user interface) and then inputting a case-type through the user interface 250. Alternatively, the system 200 may be configured to execute an automated case-type designation algorithm. For example, the system 200 may execute an algorithm that identifies information as corresponding to a predetermined information type by checking for data entries in specific fields of the received data, which specific fields are pre-determined to present specific information types; and/or the system 200 may execute an algorithm that scans all information contained in a received data set to search for specific data formatting that corresponds to a specific information type.

Again, the information contained in the received data set is not limited to only the foregoing exemplary information types [i]-[vii]; and the system 200 may be configured to both receive and identify further information types within a received data set, as well as designate received data sets with case-types specifying the presence of data corresponding to further information types.

In s303, the received data set is parsed and individual delineated anatomical structure sets 20 are identified within the computerized representations 10. The delineated anatomical structure sets 20 may include individual delineated anatomical structures 30, or groupings 40 of delineated anatomical structures 30. Suitable anatomical structures for inclusion in a delineated anatomy may include, though are not limited to: individual organs, or organ groupings; individual muscles, or muscle groupings; individual bones, or bone groupings; individual lymph nodes, chains of lymph nodes, or lymph node groupings; and etc.—and combinations of the foregoing (e.g., one or more organs together with one or more muscles and/or one or more bones). The parsing of a data set may yield multiple delineated anatomical structures sets 20, or only a single delineated anatomical structure set 20.

The parsing of a delineated anatomy is generally performed by identifying one or more delineated anatomical structures through the use of a modeling, rendering, or reconstruction of the structures. This parsing may be performed internally within the system, or by an external process with the parsed delineated anatomical structures then exported from the external process and input into the system 200. This parsing (internal or external) may be achieved using known parsing processes, such as a manual contouring interface or a process that executes an auto segmentation algorithm. In an external process, delineated anatomical structures may be input individually into the system 200, or may be input as a delineated anatomical structure set 20 with identifiers indicating individual anatomical structures (e.g., each individual delineated anatomical structure 30 within the set 20 is given a different number corresponding to an individual structure 30 which is passed with a key denoting which number corresponds to which structure 30). One example of a parsing process that may be used with the present invention is the exportation of Digital Imaging and Communications in Medicine standard ("DICOM"), radiation therapy (RT) based digital image sets as well as associated RT structure files. The enumerated delineated anatomy data inherent in the RT structure file may then be used with a computational program, such as Matlab or any number of other computational environments, to parse the delineated anatomies from the digital image data.

In s304, case-specific assessment metrics are selected for use in analyzing a delineated anatomical structure set 20. Assessment metrics that may be used in analysis of a delineated anatomical structure set 20 may include, though are not limited to: anatomy shapes; anatomy volumes; anatomy density; anatomy locations; anatomy orientations; one or more intra-anatomy distances; and etc. A collection of assessment metrics available for selection are stored in the permanent memory unit 240, and includes individual assessment metrics specific to individual anatomies (e.g., a set of shape, volume, density, and location assessment metrics for the brainstem; a set of shape, volume, density, and location assessment metrics for the brain; a set of shape, volume, density, and location assessment metrics for a brain and brainstem grouping; and etc.).

The number and type of assessment metrics chosen for use in the analysis may vary with the particular delineated anatomical structure set 20, with the most statistically relevant assessment metrics being selected for the particular delineated anatomical structures 30 in the delineated anatomical structure set 20. For example, if analyzing an delineated anatomical structure 30 having an essentially spherical shape and an asymmetrical location within the human anatomy, then an orientation assessment metric might be omitted (as it may be considered less informative of proper delineation in an essentially spherical structure), while a location assessment metric might be included (as it may be considered more informative of proper delineation in an asymmetrically located structure). In this manner, the assessment metrics selected for use in analyzing a delineated anatomical structure set 20 are case-specific to the delineated anatomical structure set 20 analyzed.

In one example, such as when the received data set does not include information presenting a sufficient anatomical designation to enable an automated selection of appropriate assessment metrics, a user may select the number and/or type of assessment metrics through the input device 250. In a manual selection of the assessment metrics, a user may view the computerized images and select appropriate assessment metrics for assessing the delineated anatomical structure set 20, delineated anatomical structures 30, and/or delineated anatomical groupings 40 that are present in the computerized images. In another example, such as when the received data set does include information presenting an adequate anatomical designation to enable the system 200 to identify appropriate assessment metrics, the processor 210 may execute an automated selection of the number and/or type of assessment metrics. In an automated selection of the assessment metrics, the system 200 will select assessment metrics that were predetermined to be appropriate assessment metrics for assessing the delineated anatomical structure set 20, delineated anatomical structures 30, and/or delineated anatomical groupings 40 that correspond to the anatomical designation presented in the receive data set. In a further example, the system 200 may be configured for both manual and automated selection of the number and/or type of assessment metrics, such that the method of selection may be selectively switched between manual and automated on a case-by-case basis; and such that a user may add manually selected assessment metrics to a group of automatically selected assessment metrics.

The selection of case-specific assessment metrics in s304 may be conditioned on one or more additional factors ("conditioning factors"). Conditioning factors may include, though are not limited to: [a] the number of computerized representations present in the received data set; [b] an anatomical designation; [c] the designated modality for the computerized representations 10; [d] patient demographics; [e] patient socioeconomic status; [f] information from patient medical history; [g] patient lifestyle factors; and any other relevant patient-specific data not directly derived from the computerized representations 10 of a patient's anatomy.

In an automated selection of assessment metrics in s304, an automated conditioning may be executed by the processor 210 based on information contained in the data set received at the processor 210. In a manual selection of assessment metrics in s304, an automated conditioning may be effected in a user's selection process by the processor 210 invoking certain restrictions on the assessment metrics available for selection by the user based on information contained in the data set received at the processor 210, and/or data entered by the user. For example, in a manual selection method, the system 200 may prompt a user to enter information relevant to one or more conditioning factors through the input device 250, and the processor 210 may then invoke certain restrictions on the assessment metrics available for selection by the user based on the user-entered information.

In s305, assessment criteria reflecting acceptable tolerances for delineated anatomy accuracy are generated and loaded into a temporary memory unit 245. The assessment criteria are generated from statistical data stored in the permanent memory unit 240. The stored statistical data includes metric standards corresponding to each of the available assessment metrics stored in the permanent memory unit 240. A metric standard will define a baseline tolerance range for a corresponding assessment metric, and will be used to judge whether a corresponding resultant metric (i.e., a resultant value generated by applying the corresponding assessment metric to a delineated anatomical contour) is within an acceptable range. For example, if the assessment metrics available for selection include: a shape metric; a volume metric; a positioning metric; and an intra-anatomy distance metric for a brainstem, then the stored statistical data will include metric standards for each of the shape; volume; positioning; and intra-anatomy distance for a brainstem.

The metric standards in the stored statistical data may equate, one-to-one, with the assessment criteria such that generation of assessment criteria requires only identifying the metric standards in the stored statistical data that correspond to the selected assessment metrics. Alternatively, the stored statistical data may include one or more metric modifiers, and generation of assessment criteria may include identifying the metric standards corresponding to the selected assessment metrics, identifying one or more metric modifiers, and then adjusting one or more of the metric standards with the one or more metric modifiers.

A metric modifier is a parameter that will modify the baseline tolerance range defined by a corresponding metric standard, such that the modified tolerance range defined by the modified metric standard more appropriately corresponds with the case-specific assessments being made for a particular data set received at the system 200 (e.g., the modified tolerance range will define more suitable ranges for the specific patient, specific anatomies, specific imaging modalities, and etc.). Metric modifiers may include parameters that are predetermined to provide suitable modifiers based on particular case-type information including, but not limited to: [I] modality data of the computerized representations 10; [II] demographic data; [III] socioeconomic data; [IV] medical history information; [V] lifestyle factors; and etc.

In s305, a determination is made as to what delineated anatomical structure set 20, delineated anatomical structures 30, and/or delineated anatomical groupings 40 are being assessed in the computerized images. This may be done by: referencing one or more anatomical designations presented in the received data set; referencing the user-entered information designating one or more anatomies during a manual selection of assessment metrics in s304; and/or referencing the specific assessment metrics that were selected in s304.

Once an anatomical designation or specific assessment metrics is identified, one or more corresponding metric standards are selected.

Once a set of metric standards is selected, a similar determination and selection is made for a set of metric modifiers. This determination and selection of appropriate metric modifiers may be done by: referencing one or more information types presented in the received data set (e.g., the information types [i]-[vii]); referencing data from a user-entry during a manual selection of assessment metrics in s304; and/or referencing the specific assessment metrics selected in s304.

As one example, generation of a volume assessment criterion for a patient's brainstem may include determining that a brainstem is an anatomy to be assessed in the computerized images (either by referencing an anatomical designation in the received data set, referencing a user-entered selection of the brainstem anatomy, or referencing a selected assessment metric corresponding to the brainstem), and then identifying in the stored statistical data a volumetric standard for a brainstem. A further determination is then made as to whether the received data set contains any further information types that may necessitate an adjustment to the tolerances defined by the volumetric standard for the brainstem. If, in this example, it is determined that the received data does contain both demographic data (e.g., gender=male) and socioeconomic data (e.g., occupation=firefighter), then there will be identified in the stored statistical data a corresponding demographic modifier (e.g., a "male" parameter) and a corresponding socioeconomic modifier (e.g., a "firefighter" parameter). The volumetric standard for the brainstem will then be adjusted by both the "male" demographic modifier and the "firefighter" socioeconomic modifier to calculate a modified volumetric standard that will be used as an assessment criteria for the brainstem contouring. Once such an assessment criterion is generated, it is loaded into a temporary memory unit 245.

Each assessment criteria (AC) is generally defined as a window of acceptable values around some metric standard (MS). Thus, one example of an assessment criteria (AC) may be characterized by the following relationship (1):

$$MS-W1<AC<MS+W2 \quad (1)$$

given, W1>0; and
W2>0.

In the foregoing relationship (1), the values W1 and W2 are boundary values establishing window boundaries of the acceptable values to be defined by the corresponding assessment criteria. In this relationship, W1 may or may not equal W2. The assessment criteria and window boundary values may then be modified based on different category modifiers (such as the gender/occupation modifiers of "male/firefighter" described in the foregoing example).

Multiple approaches may be used to modify the assessment criteria and window boundaries. In one aspect, a tabular approach may be used wherein a different set of assessment criteria parameters (given as MS, W1, and W2 values; as AC bound values alone; as MS values+/−a symmetric window; and etc.) exist for each distinct cohort of modifiers. Following the example above, one set of tabulated assessment criteria parameters may be used for the case of "male/firefighter", while another set of tabulated assessment criteria parameters may be used for "female/firefighter". In another aspect, a model based approached may be used wherein a baseline set of assessment criteria parameters are determined and then one or more metric modifiers are used to adjust the basic parameters, as illustrated by the following exemplary relationship (2):

$$[\alpha^*\beta^*\gamma^* \ldots ]^*MS-[a^*b^*c^* \ldots ]^* \\ W1<AC<[\alpha^*\beta^*\gamma^* \ldots ]^*MS- \\ [a'^*b'^*c'^* \ldots ]^*W2. \quad (2)$$

In the forgoing relationship (2), each metric modifier ($\alpha$, $\beta$, $\gamma$, ... a, b, c, ... or a', b', c', ... ) correlates to a specific modifier category. As such, in the example above, "male" may be a baseline gender parameter (a=a=a'=1), while for the "female" gender these values may all be different (and need not be equal).

The initial assessment criteria parameters (including modifiers, if used) can be determined in a number of different ways, including, though not limited to: heuristically; from one or more initial input datasets; from one or more model-based approaches (mathematical, computer-vision-based, etc.); and etc.; or combinations of one or more of the foregoing. One example of a heuristic approach may be to input a "known" guess, such as a rough estimate of the typical volume of the human brain, and using one or more input dataset, statistical, computer-vision-based, or other approaches to extract the assessment criteria parameters. Meanwhile, one example of a model based approach may be to use a known mathematical relationship between weight and head diameter to determine the weight modifier for the assessment criteria parameters for a brain volume. In all cases, the feedback portion in s314-s316 will allow for the assessment criteria parameters to be adjusted and optimized through a number of different approaches (e.g., user adjustment; machine learning; neural network computation; and etc.).

The stored statistical data may take a number of forms. In one example, the stored statistical data may be general-population data (e.g., statistical data based on the general human population), or local-population data (e.g., statistical data based on a target population within a given geographic range of an individual system 200). The general or local ("general/local") population data may be pre-loaded into the permanent memory unit 240 either prior to delivery of the system 200 to an end-user, or by an end-user during an initial set-up of the system 200. In another example, the stored statistical data may be specific-population data which has been recorded to the permanent memory unit 240 of an individual system 200 from analyses made during one or more executions of the process 300 by that individual system 200.

In s306-s308, the processor 210 executes an analysis of a delineated anatomical structure set 20 parsed from the data set in s303. In particular, in s306, a further parsing process is executed relative to the delineated anatomical structure sets 20 to parse out and identify a first delineated anatomical structure 30 or delineated anatomical structure grouping 40 ("parsed anatomy 30/40") within the delineated anatomical structure set 20. This further parsing process may be executed in a similar manner, and using similar resources, as the parsing operation in s303 for parsing individual delineated anatomies in the computerized representations.

Then, in s307, the processor 210 executes an analysis of the first parsed anatomy 30/40 by applying each relevant assessment metric selected in s304, and generates a resultant metric for each applied assessment metric, and stores the resultant metrics in the temporary memory unit 245.

Resultant metrics can be binary type or statistical type. A binary-type metric is one that has two potential values (e.g., yes/no; right/left; and etc.). A binary type metric would be used, for example, to assess if one anatomical structure is contained within another, such as to address if, in the delineated anatomy, the brain is wholly contained within the skull. Statistical type metrics have a range of values; and may include, but are not limited to: size assessments; shape assessments; positional assessments; imaging data based assessments; and etc. Such resultant metrics may be generated from the computerized representations using pixel recognition algorithms to assess, for example, pixel count; pixel intensity and location; and intra-pixel distance.

An example of a size assessment is volume. In a DICOM-based CT dataset, for example, the size (volume) of an individual pixel may be determined from the image file header. Then, by counting the number of pixels within a delineated anatomy, and multiplying it by the volume of an individual pixel, the volume of the delineated anatomy can be calculated, with adjustments made for individual pixels which may be partially along the edge of structures (e.g., if a pixel is deemed to be "halfway" within a structure the algorithm may count only half of the pixel volume towards the structure volume).

An example of a shape assessment metric could be circularity (how close an object is in shape to a circle). In a planar image (a slice from a CT, MR, or a 2D radiograph), for example, the size (length) of an individual pixel may be determined, which provides the center-to-center distance between pixels, potentially from the DICOM header. From this data, the distance between the two furthest separated pixels in a structure can be determined, and the area of a circle may be calculated using this distance between furthest pixels as a diameter of the circle. Counting the number of pixels in the structure from the planar image, and multiplying the number of pixels by the pixel size gives the true area. A ratio of the area calculated by using a furthest-pixel approach to the area calculated by a pixel count approach may then be used to determine how circular an object is.

An example of a positional assessment metric could be the center-to-center distance between two structures. Given the position of each pixel within a delineated anatomy in an image, the center of mass of the structure could be calculated. As above, using the pixel size (length and/or center-to-center distance) within the image, along with the number of pixels between the centers of mass of two structures, the center-to-center distance between the structures can be calculated.

An example of an imaging data based metric could be the average density of the structure. For example, in a CT dataset, the Hounsfield Unit (HU) value of each pixel within a delineated anatomy could be used to determine the density of the object identified within that pixel. By averaging the HU of all pixels within a structure, the average density could thus be determined.

In s308, after recording a resultant metric for each assessment metric applied to the first parsed anatomy 30/40, the processor 210 judges whether each resultant metric satisfies the corresponding assessment criterion that was stored in the temporary memory unit 245 during s305. If a resultant metric is judged to satisfy its corresponding assessment criterion, then a positive judgment is recorded; and if a resultant metric is judged to not satisfy its corresponding assessment criterion, then a negative judgment is recorded. The foregoing judgment of resultant metric relative to a corresponding assessment criterion is performed for each resultant metric generated in s307 and the judgment results are stored in the temporary memory unit 245.

The foregoing sequence of s306-s308 is repeated for each remaining parsed anatomy 30/40 in the delineated anatomical structure set 20; until, in s309-s311, the sequence is completed for the final parsed anatomy 30/40 in the delineated anatomical structure set 20 (i.e., the $N^{th}$ parsed anatomy in the delineated anatomy). Likewise, the sequence of s305-s311 is repeated for each delineated anatomical structure set 20 identified in s303; until in s309-s311, the sequence is completed for the final parsed anatomy 30/40 in the final delineated anatomical structure set 20 (i.e., the $N^{th}$ parsed anatomy in the $N^{th}$ delineated anatomical structure set). Alternatively, instead of repeating the s305 for each iteration of s306-s308 through s309-s311, the assessment criteria for all structures in all iterations s306-s308 through s309-s311 could be loaded in a first execution of s305; and thereafter each iteration from s306-s308 through s309-s311 could be performed by merely returning to the beginning step in each respective iteration (e.g., begin with s306, s309). In a further alternative, the repetition of further iterations could also require repeating step s304, in addition to step s305, in each iteration from s306-s308 through s309-s311.

The sequences s306-s308 through s309-s311, for the individually parsed anatomies 30/40, may be executed in sequence or in parallel. Likewise, the repetitions of the sequence s305-s311 (or s306-s311; or s304-s311), for the individually delineated anatomical structure set 20, may be executed in sequence or in parallel.

In s312, after a judgment result has been recorded for each resultant metric in each parsed anatomy 30/40, from each delineated anatomical structure set 20 parsed from the received data set, the system 200 determines if any negative judgments were recorded in s308.

If one or more negative judgments are detected, then the system assesses the quantity and type of resultant metrics producing the negative judgment and determines whether it deems there to be one or more errors in the delineated anatomical structure set 20 of the computer representations 10. If the system determines that errors exist in the delineated anatomical structure set, the process proceeds to s313 in which a quality assessment report is generated providing details of the errors.

Depending on the anatomical structure set 20, specific delineated anatomical structure 30, anatomical structure grouping 40 and/or the selected case type, the system may be designed to accommodate specific combinations or amounts of negative judgments to assess whether an error exists. The quality assessment of an individual delineated anatomical structure may be of a simple binary type (e.g., the structure is correct or incorrect) or, alternatively may be probabilistically assessed, in that if there is a high degree of positive judgments there is high certainty the delineated anatomical structure is correct while if there is a high degree of negative judgments there is high certainty the structure is incorrect (e.g., there is an 80% chance the structure is incorrect).

The quality assessment report generated in s313 may include, but is not limited to: a complete list of the assessment metrics together with a listing of the corresponding resultant metrics, corresponding assessment criteria, and corresponding judgment results; a list of delineated anatomical structure set 20 for which an error was detected (i.e., a negative judgment between one or more resultant metrics and a corresponding assessment criterion); a list of parsed anatomies 30/40 for which an error was detected; and detailed information for each detected error. Detailed information that is included in a quality assessment report generated in s313 for a detected error may include, though is not limited to: the resultant metric deemed to have generated an error; the difference(s) between the resultant metric and the corresponding assessment criterion; a description of potential sources for the error; and one or more suggested actions for potentially correcting the error.

In s314, the quality assessment report generated in s313 is output to a user via a graphical user interface (e.g., the GUI of the input device 250, or another GUI) and/or a reproduction device 260 (e.g., a printer), so that a user may review and evaluate the quality assessment report in s315. If the system 200 does not detect any negative judgments in s312, then the process proceeds to s314 without performing s313. A quality assessment report generated by proceeding from s312 directly to s314 may simply indicate that no errors are detected; or it may provide all the same data fields as a report generated from s313 would provide, though showing all positive results and omitting any suggestions for error sources and corrections.

In s315, a user evaluates the quality assessment report from s314 to determine if the delineated anatomical structure set 20 within the computerized representations 10 are valid and accurate. If the user determines that the delineation validity and/or accuracy are poor, then the user may take actions either to correct the delineated anatomical structure set 20, or to generate new computerized representations 10 of the patient's anatomy. If the user determines that the validity and accuracy is good, then the user may approve the delineated anatomical structure set 20 for use in a medical procedure.

In addition, if the user deems the resultant metrics generated in s307 to s310 to be valid and accurate representations of a target population, then the user may approve the resultant metrics for permanent recordation. If permanently recording a set of resultant metrics, the process 300 proceeds to s316, wherein the resultant metrics are recorded to the permanent memory unit 240, and the process 300 thereafter ends. Alternatively, if the user deems the resultant metrics generated in s307 to s310 to be not valid and/or not accurate representations of a target population, then the user may forego or deny permanent recordation of the resultant metrics, in which instance the process 300 ends without performing s316. The system 200 may be configured to proceed, as a default, to s316 and permanently record resultant metric data unless a user affirmatively denies recordation at s315. Alternatively, the system 200 may be configured to proceed, as a default, to end the process 300 after s315 without recording the resultant metric data unless a user affirmatively chooses to record the resultant data.

The recordation of resultant metrics to the permanent memory unit 240 facilitates an operation of the system 200 though learned statistical data. In particular, the system 200 may use general/local population statistical data during initial executions of the process 300, and then subsequently switch to specific-population statistical data after having permanently recorded resultant metrics from a predetermined number of executed processes 300. After switching to specific-population statistical data, the system 200 may continue to adjust and refine the specific-population statistical data through the recordation of further user-approved resultant metrics. Alternatively, the system may discontinue the recordation of user-approved resultant metrics after switching to the specific-population statistical data.

In another example, the system 200 may operate based on refined statistical data that is generated by adjusting the preloaded general/local population statistical data itself. In particular, as with the foregoing example, the system 200 may be preloaded with general/local population statistical data, and configured to selectively record user-approved resultant metrics from executions of the process 300. However, in this example, the user-approved recorded resultant metrics are not used to generate a separate collection of specific-population statistical data; but, instead, are used to update and refine the preloaded collection of general/local population statistical data. The refined statistical data (i.e., the general/local population data that has been updated and refined by specific-population data) is then used to generate the assessment criteria in subsequent executions of the process 300.

Experimental Testing

A prototype was created and used to analyze an array of randomly selected delineated anatomical structures in a delineated anatomy that had clinically relevant errors inserted into the delineated anatomical structure. The prototype was configured to search for errors in the contours by looking for outliers according to a programmed set of rules. The rules were established by an independent, randomly-selected professional in the field of anatomical contouring, and verified for correctness by an expert prior to analysis. The prototype was blinded to the number, type, and location of the errors. During testing, the prototype detected nearly all of the contour errors with limited numbers of false positives.

In particular, normal tissue contours from 29 patients being treated for head and neck cancers were selected based on adherence of the patient's contours to clinical guidelines. For each patient, a DICOM plan and anatomical structure files were exported from the treatment planning system to an in-house software program, which calculated resultant metrics for volume, shape, and intra-structure distances for all anatomical structures. A statistical analysis of the resultant metrics produced seven suitable statistical-type metrics that were used within the software program to evaluate the accuracy of head and neck contours from other patients. Six of these seven statistical-type metrics were: volume; number of image slices (the total number of axial images in which a structure appeared); mean minor axis and mean major axis (the widest horizontal and vertical extent of the object); mean slice eccentricity (ratio between the major and minor axis on each axial image in which a structure appeared); and mean slice area (average area of structure on each axial image in which it appeared). The seventh statistical-type metric was the family of center-of-mass-to-center-of-mass distances for each structure analyzed.

Figure 4:
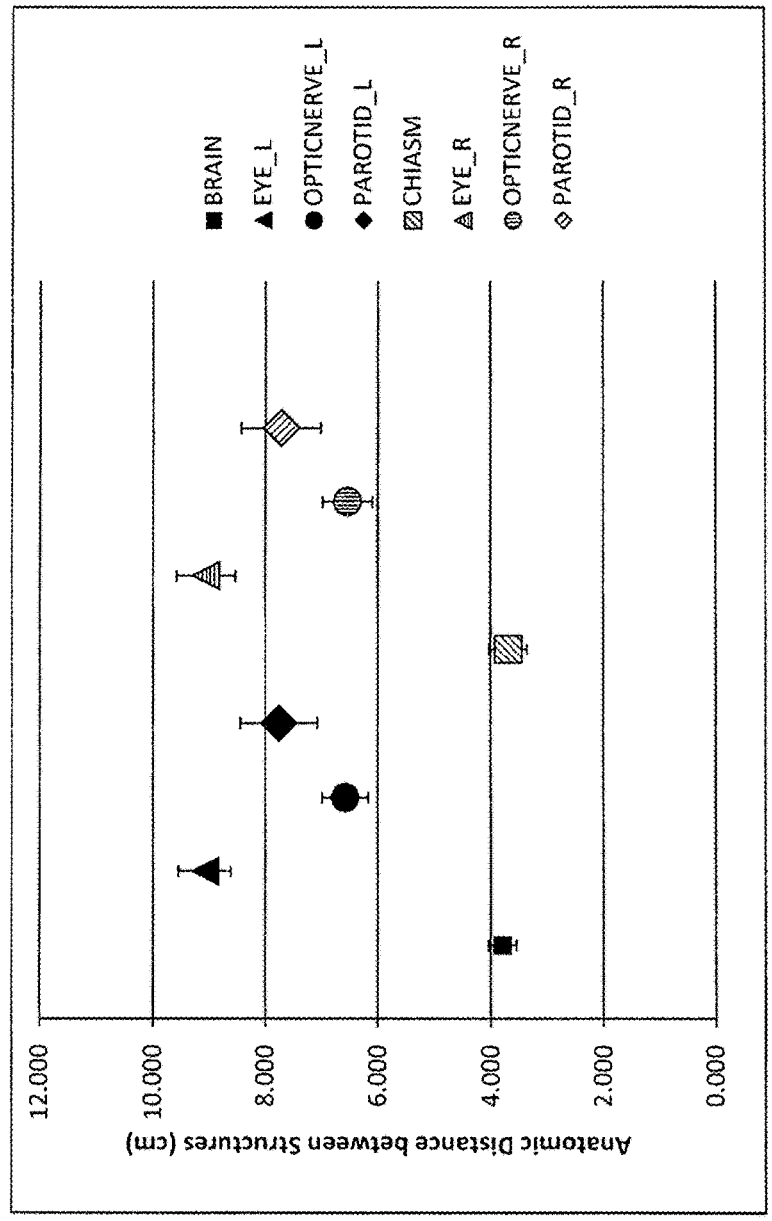
FIG. 4 illustrates measured distances between anatomic structures, as determined by an application of the present invention in evaluating the accuracy of the contour's in an anatomical structure.

The mean distance between the geometric centroids of each anatomical structure proved to be a useful metric for evaluating the accuracy of a contour's anatomic position, as shown by the results in FIG. 4. In particular, FIG. 4 illustrates one example of center-of-mass-to-center-of-mass distances wherein a number of centroid-to-centroid distances as measured from the geometric centroid of the brainstem to the geometric centroid of a number of surrounding structures. The symbols in the chart of FIG. 4 show the centroid-to-centroid distance measured relative to the corresponding structure in the accompanying legend. The error bars extending from each symbol in the chart show the 1.96x standard deviation of the particular centroid-to-centroid distance, which also represents the assessment criterion for an intra-anatomy distance for the brainstem. Although this example illustrates an intra-anatomy metric measured as a centroid-to-centroid distance, it is to be understood that an intra-anatomy metric may be measured between points other than the centroids. For example, an intra-anatomy metric could be a measurement of the distance between the two closest points in two anatomical structures, the distance between the two furthest points in two anatomical structures, or a combination of distances measured between multiple points of two anatomical structures.

As shown in Table 1, the accuracy of a contour's shape and size was assessed by examining each anatomical structure's volume, major and minor axis (averaged over all axial planes), mean eccentricity, number of image slices, and the mean area of the contour in an axial plane.

TABLE 1

Size and shape metrics used for the Brainstem contour evaluation. The upper and lower bound were calculated as 1.96 × standard deviation, with 95% of all measured metrics expected to fall within this range.

| Metric | Lower Bound | Mean | Upper Bound |
|---|---|---|---|
| Volume (cc) | 16.16 | 24.11 | 32.06 |
| Number of Slices | 15 | 20 | 25 |
| Mean Minor Axis (cm) | 1.71 | 2.02 | 2.33 |
| Mean Major Axis (cm) | 2.05 | 2.41 | 2.78 |
| Mean Slice Eccentricity | 0.381 | 0.495 | 0.61 |
| Mean Slice Area (cm$^2$) | 2.873 | 4.03 | 5.19 |

It is noted that the contour assessment program only included selected assessment metrics for which the standard deviation was less than a heuristically determined limit of 15% of the mean for that assessment metric. To verify the software's utility, 42 common contouring errors were intentionally introduced within 9 specific structures, for 9 different patients. The inserted errors included incorrect laterality, position, size, and shape; the inclusion of small isolated pixels; the deletion of segments; and empty structures (e.g., named, listed, and/or expected delineated anatomical structures for a given case type that had not been delineated).

The evaluation of all 9 head and neck structure sets was completed without prior knowledge of the nature or number of the generated errors. Table 2 shows summary of results from the validation tests of the contour assessment software program. It is noted that, further to the seven statistical-type metrics described above, the following five additional binary type metrics were also analyzed: deleted contour (if the contour of interest existed in the dataset); deleted slice (if the structure was present on non-contiguous axial images); laterality switched positioning (if the contour was correctly on the right or left side for asymmetric structures such as the left eye); small ditzels (were noise pixels or "ditzels" contoured accidentally outside of a structure present); and continuity of structure (was a structure continuous within an axial image).

In Table 2, "true events" were those implemented by a user into one of nine contours in one of nine patient contour sets. As can be seen from the tabulated data, the total number of true positive events is greater than 95% while false positives remained relatively low. It is noted that the upper and lower bounds should be optimized to eliminate any false negatives, minimize fall positives, and identify as many true events as possible.

TABLE 2

Results from evaluating the statistical population-based contour assessment software program.

| Error Type | True Events | True Positive | False Positive | False Negative |
|---|---|---|---|---|
| Volume Modification | 8 | 7 | 5 | 1 |
| Location Modification | 4 | 4 | 1 | 0 |
| Shape Modification | 10 | 9 | 3 | 1 |
| Deleted Contours | 4 | 4 | 0 | 0 |
| Deleted Slice (Gap) | 6 | 6 | 0 | 0 |
| Laterality Switched | 3 | 3 | 0 | 0 |
| Small Ditzels | 6 | 6 | 0 | 0 |
| Continuity of Structure | 1 | 1 | 0 | 0 |
| Total | 42 | 40 | 9 | 2 |

The introduced errors represent common contouring mistakes and were implemented on high priority planning contours (brain, brainstem, optic chiasm, right/left eyes, right/left optic nerves, and right/left parotid glands). Volume and shape errors ranged from small deviations in the optical contours to large expansions within an individual slice created using automatic contouring tools. Positional errors were tested by mislabeling the contours (i.e., submandibular glands as parotid glands) and expanding contours non-uniformly in one direction. The accuracy of a contour's laterality and continuity (existence of gaps or small, isolated pixels) was also tested.

In the results of Table 2, a contour was considered inaccurate if it failed more than 2 of the statistical-type metrics or any one of the binary-type metrics. Again, the prototype proved highly effective in that it correctly identified 40 of 42 generated errors; a success rate of over 95%. It was observed that small modifications to anatomical structure's shape and volume were the most difficult to correctly identify, with false positive responses occurring for small changes in a contour's volume and shape. However, the program correctly identified all positional and laterality errors, deleted/isolated segments, small pixels, and deleted contours. Furthermore, though not wishing to be bound by theory, it is expected that analysis results will improve, and false positive responses will be minimized, upon refining the stored statistical data with a larger patient sample size; and thereby enabling the generation of more specific assessment criteria through optimized population data (e.g., adjusted upper and lower bounds for each assessment metrics, with metric modifiers for gender, age, disease situs, etc.).

The foregoing test results from the prototype confirm that rules developed from a statistical analysis of anatomic population-based metrics can provide the necessary information to correctly and efficiently evaluate the accuracy of a unique patient contours in computerized representations of patient anatomies (e.g., delineated anatomies and parsed anatomical structures), such as those generated during an online adaptive radiation therapy protocol. The present invention provides a system and process that are not limited to any particular imaging modality, and may be adapted for any chosen modality or any plurality of modalities. Likewise, the system and process are not specific to any vendor-based program or software package. As such, given the increasing complexity of medical procedures, which is expected to accelerate moving forward, and the increased dependence on multiple modalities of digital imaging for treatment planning and development, a system and method such as the present invention provides an efficient method to assure the validity and accuracy of anatomical structures extracted from medical imaging which is expected to be pivotal in imaging analysis.

For example, the present invention may be employed in a number of applications in various fields of medical practice, including radiation oncology for treatment plan development and evaluation; adaptive radiation therapy treatment and evaluation; radiology where computer-aided detection and diagnosis algorithms analyze digital medical images; and the quality assessment of computerized representations of denoted anatomical structures generally.

As one example of the application of the teachings of the present invention, in radiation oncology, volumetric patient images, typically with either computed tomography (CT) or magnetic resonance (MR), may be used to create a treatment plan. On modern radiation therapy external beam treatment machines, volumetric imaging (either CT or, more recently, MR) may be used at various points throughout the course of treatment to set up the patient correctly, as well as to potentially assess any anatomical changes, by comparing these "on-treatment" images to the original volumetric images. The use of these on-treatment images to alter a treatment plan is referred to as "adaptive radiation therapy" (ART). If this on-treatment image evaluation, plan alteration, and altered plan delivery is done while the patient is on the treatment table, this becomes "on-line adaptive radiation therapy" (OL-ART). The development and implementation of OL-ART is important due to the fact that patient anatomy may change shape or position throughout the course of treatment, either during an individual treatment, day-to-day, or over longer periods of time (week-to-week, etc.).

Figure 6:
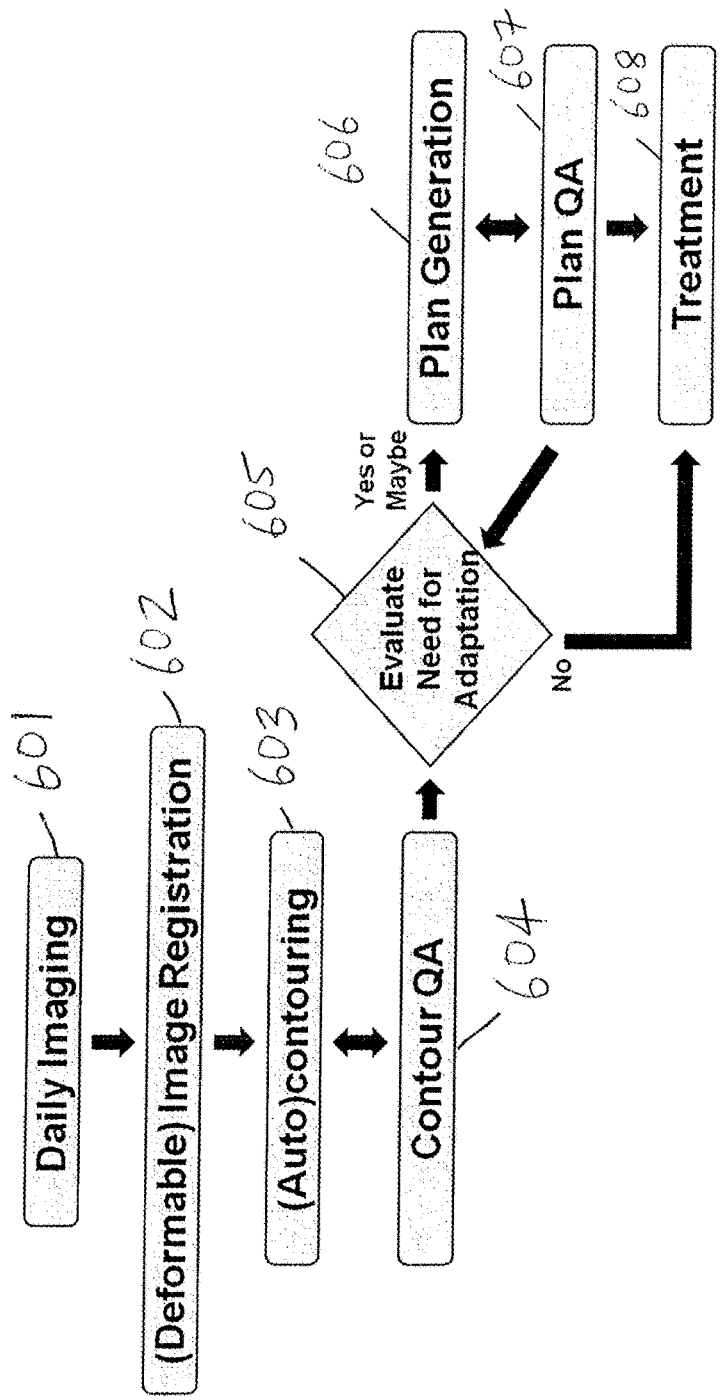
FIG. 6 illustrates a typical on-line adaptive radiation therapy (OL-ART) workflow.

A typical OL-ART workflow is shown in FIG. 6. In s601, on-treatment daily images are acquired of the patient setup in the treatment position. In s602, these on-treatment images are manually and/or automatically registered to the original volumetric images using rigid or deformable image registration techniques. In s603, the patients tissues and/or organs are contoured either manually and/or automatically. In s604, the accuracy of the contours is validated using the methodology described by the present invention. In s605, the need to adapt the radiation treatment plan is determined by evaluating the impact of delivering the current radiation treatment to the current daily shape and positions of all contours, with this detailed process diagrammed in FIG. 7. If s605 determines that the current positions/shapes of the contours requires a plan adaption, a new radiation treatment plan is generated in s606. In s607 the quality of the new radiation treatment plan is evaluated for deliverability after which further adaptations may be considered by returning the new plan to s605. If s605 determines that the proposed radiation treatment plan will accurately, within some margin, deliver the intended dose to all contours, the workflow proceeds to s608 and the radiation is delivered.

One previous limitation to widespread implementation of OL-ART lies in the time it takes to perform all of these steps. With extensive time there is greater chance that patient anatomy could change or the patient may themselves move, invalidating the accuracy (and potentially efficacy) of the updated plan. Automation could reduce the time at each stage, but previously has not been developed for all the steps of FIG. 6. In the absence of an automated process, contours must be evaluated manually, a time consuming and error-prone task due to a number of human factors.

The process as described above seeks to determine if an evaluated contour is correct based on metrics extracted from a population of similar contours. There is also commercial software (StructSure, Standard Imaging Inc.) which attempts to determine if a contour matches some reference contour (such as a "population average" reference or contours from a previous scan of the patient in question). However, neither approach is sufficient for OL-ART, where you need to evaluate both the accuracy of the original / modified contour and if any modifications could impact the quality of the current treatment plan, motivating possible changes in the treatment plan. This is due to the fact that, as discussed earlier, patient anatomy can change or move between treatments (examples include changes in filling status of the bladder, or warping/ movement of parotid glands relative to other organs (Barker et al. IJROBP 2004)). Matching to a reference is insufficient, as a contour can move or warp relative to the reference and still be correct. Furthermore, solely establishing if the contours are correct does not provide the necessary information to determine the dosimetric impact resulting from possible changes to the contour. The decision tree necessary for evaluating structures for OL-ART is thus three tiered, with different action levels depending on the answer to questions, as shown in FIG. 7.

Figure 7:
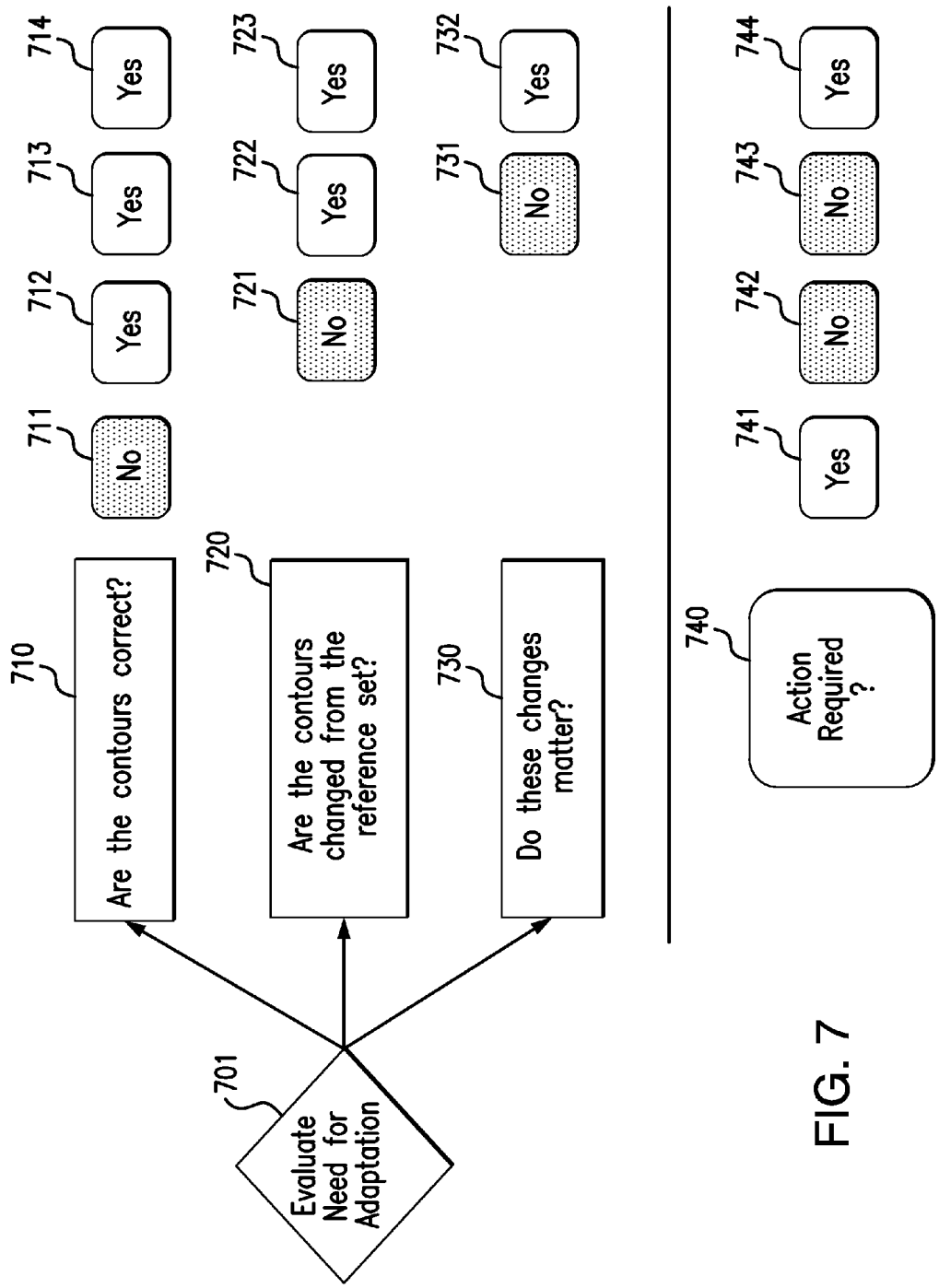
FIG. 7 illustrates an exemplary decision tree that may be used to evaluate structures for OL-ART.

With reference to FIG. 7, s701 represents the evaluation process for adaptation of a radiation treatment plan as diagrammed in s605 in FIG. 6. This evaluation is a three tiered process and is performed by determining the status of three states for the daily patient treatment, shown as s710, s720, and s730. Depending on the specific combination of states of each status as shown in each column of FIG. 7, the evaluation process determines if an action is necessary, as seen in s740. In s710, the accuracy of the daily contours are evaluated using the apparatus and methodology of the present invention. If the contours are not correct (s711), then an action is required, as indicated in s741. Steps 712, 713, and 714 indicate the contours are accurate and the evaluation continues to the second state (s720) which evaluates if the daily contours have changed compared to the original reference data set. If the contours have not changed relative to the reference data set (s721), then no action is required (s742). In steps 722 and 723, the evaluation process has determined the daily contours are different compared to the reference data set and the process continues to the third state, which determines if these difference will matter for the for the accuracy of the patient's treatment (s730). If these changes will not impact the accuracy of the patient's treatment (s731), then an action is not required (s743). If the changes will impact the treatment accuracy (s732), then action is required (s744).

A process for evaluating contours in an OL-ART scenario is thereby provided. The fundamental formula for evaluating the correctness of contours in this process is defined by:

$$[Rules] = \{\alpha[Population] + \beta[Patient] + [binary]\}$$

where [Rules] are a set of discrimination values used to assess a series of tabulated statistical metrics for new (input) structures against a population distribution (the "knowledge base") of those metrics (the [Population] set of rules in the equation above).

In an OL-ART process, imaging (contour) data for an individual patient may be collected regularly (daily, weekly, etc.). This data could thus be used to refine the discrimination criteria with "patient specific" rules, denoted above by [Patient]. $\alpha$ and $\beta$ are variable coefficients ($\alpha+\beta=1$) initially weighted towards the population rules (i.e. $\alpha>\beta$); as more patient data is collected $\beta$ can be increased and $\alpha$ can be decreased (potentially to 0). The values of $\alpha$ and $\beta$ can be changed over time to depend on the amount and usefulness of the patient data.

In the formulation above [binary] describes those rules which are not statistical in nature, in that they are characteristics that can be answered with a simple yes or no question (Example: Is the laterality of structure X correct?). Such rules do not thus change with the amount or quality of data collected.

Next, to determine if a structure has changed, a set of statistically-based criteria may be applied to metrics determined from the contours collected on a given day to compare them to metric values tabulated on the first day of treatment. A second set of criteria could then be applied to determine if these differences are dosimetrically important. These criteria can either be population based, or derived from information from the patient-specific data (similar to the methodology described above). Note that these two steps (steps 720 and 730 from FIG. 7) could be combined (one threshold that seeks to determine if a change is dosimetrically significant could be applied), but may not necessarily be so (an example would be a structure whose change may not be currently important for the plan dosimetry, but that may be useful to track to see if changes in it become important at some point, or to track the radiation dose for evidence-based medicine study endpoints).

Interest in facilitating clinical implementation of OL-ART is at an all-time high and increasing rapidly, and the present invention serves to further enable OL-ART. New technologies such as the ViewRay device from ViewRay, Inc which provides integrated MR imaging and radiation therapy treatment delivery technologies, are starting to be implemented clinically, and we are getting closer to seeing clinically viable MR-integrated into medical linear accelerators, and the use of on-board computed tomography is becoming increasingly widespread. Any of these systems may use an automated contour review system, such as provided by the present invention, to actuate a clinically feasibly broad-scale implementation of OL-ART. The teachings of the present invention may be developed and sold as a stand-alone software tool, or licensed to any number of vendors for integration within their radiation treatment planning and/or delivery system.

The automated contour evaluation system described herein is expected to limit human error and substantially reduce the inter-user and intra-user variability in contour creation and evaluation, as well as enhance the efficiency of treatment planning quality assurance. In addition, although the average human size varies due to a number of factors (including demographics, socioeconomic status, etc.), the present invention is capable of accounting for these differences by providing the individual system 200 with stored statistical data that is relevant to the particular patient population for which that system will be employed. As such, the disclosed system and method are expected to lead to better quality treatment plans, and greater clinical throughput, with an analysis that is tailored to the specific population served.

Alternate Embodiment Using Geometric Attribute Distribution Models

Figure 9:
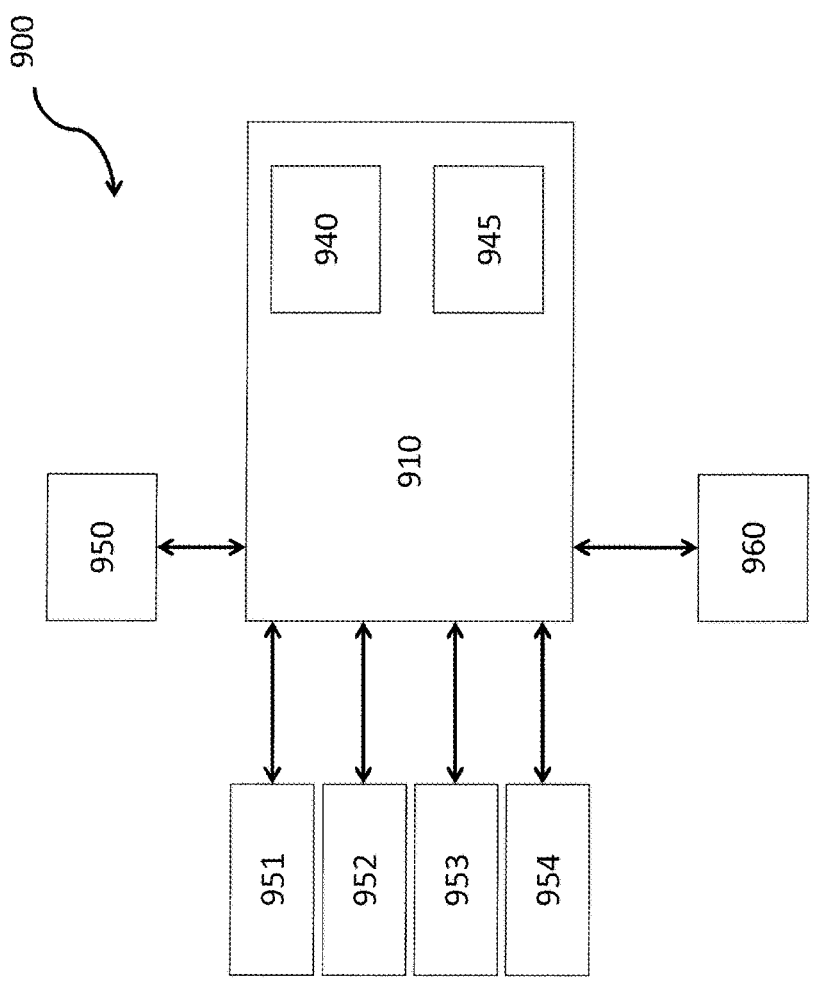
FIG. 9 illustrates a system for use in performing the process of FIG. 1.
Figure 10:
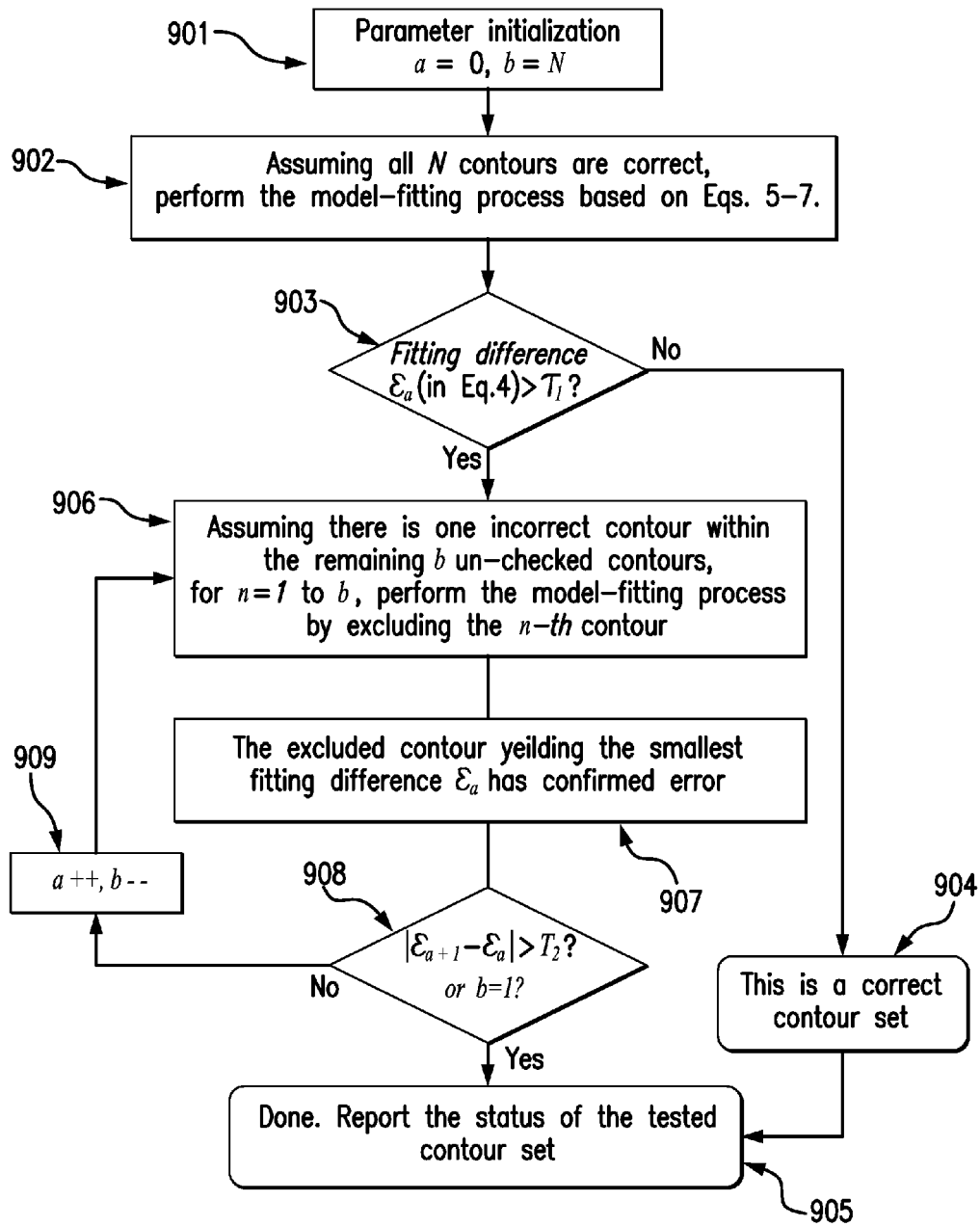
FIG. 10 illustrates the iterative weighted interstructural GAD model-fitting process.

FIG. 9 illustrates a system 900 for use in performing the processes 800. The system 900 includes a processor 910 for receiving input data, either in the form of a completely compiled data set, or in the form of individual data packets, which may subsequently be compiled into a data set. The processor 210 may include permanent memory 940 and a temporary memory 945.

An input device 950 (e.g., a graphical user interface) is connected to the processor 910, and configured for a user to control the processor 910 and for a user to selectively enter data into the processor 210. A user may employ the input device 950 to control the processor 910 in executing the process 800. In addition, a user may employ the input device 950 to enter information to the processor 910.

A user's entry of information to the system 900 may be dependent entirely on user discretion, or it may be responsive to automated queries generated at the input device 950. In some examples, the system may also communicate with an output device 960 for reproducing information that is displayed to a user through the input device 950. Both the input device 950 and the output device 960 may be a part of the system 900 (e.g., a localized input device with the system), or one or both may be external to the system and connected over a network.

One or more additional input devices 951-954 may also be connected to the processor 910. The additional input devices 951-954 may each provide a specific information type to the system 900.

Additional input devices 951-954, etc. may communicate with the processor 910 to provide additional information. Each of the input devices 951-954, etc., may be either geographically remote from the system 900, or locally-remote (e.g., inter-departmental within a common facility); and each communicating with the system 900 over a network.

Figure 8:
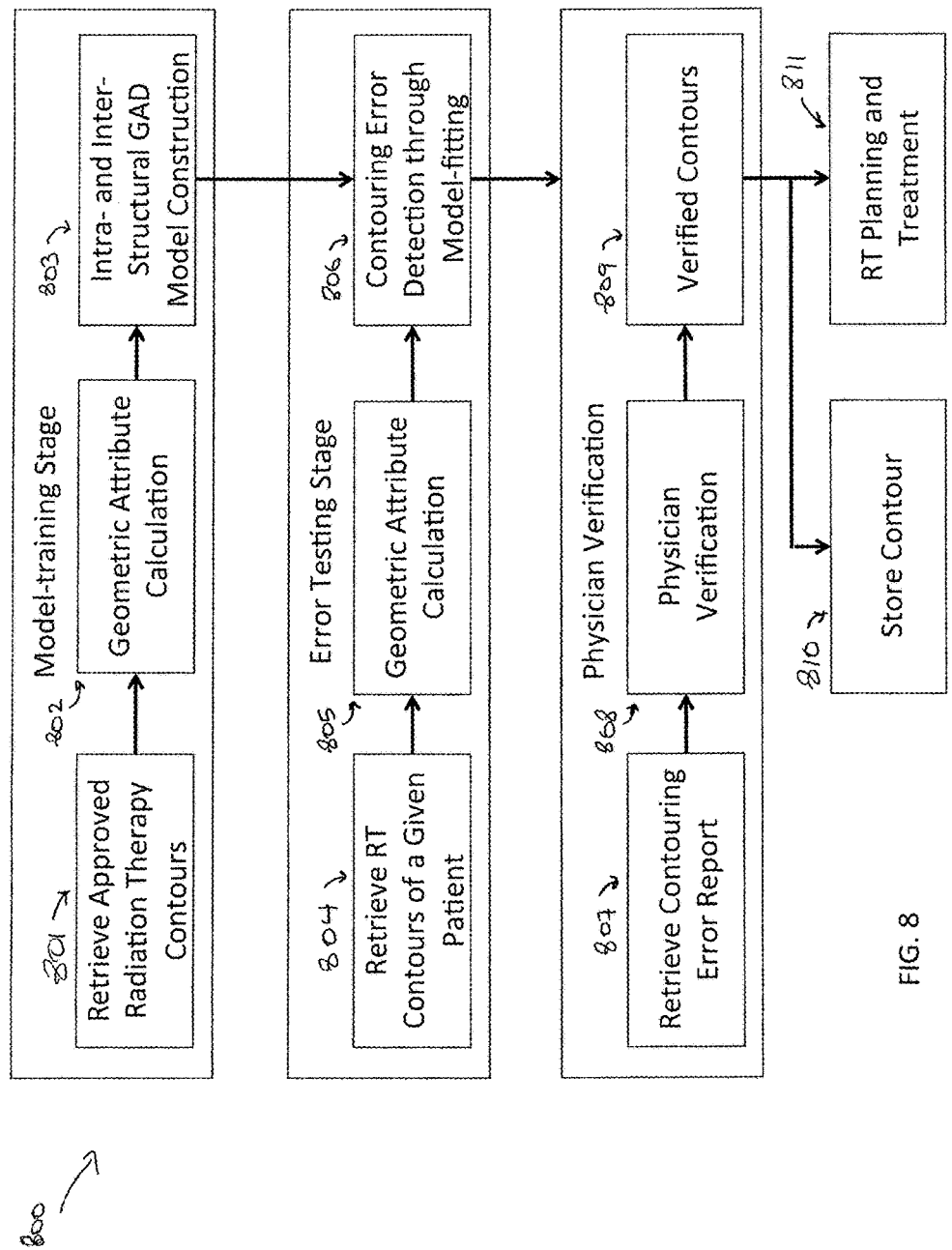
FIG. 8 illustrates a generalized process for automated quality control of computerized representations of human anatomy.

FIG. 8 illustrates a general process 800 for assessing the delineation accuracy of one or more delineated anatomies in a computerized representation of a patient's anatomy and using the delineation in a radiation therapy treatment. The steps of the process are categorized as model-training stage, error-testing stage, and physician verification stage. Step s801, s802, and s803 are part of the model-training stage. In the model-training stage, a number of patient cases with approved contours are utilized as the training sets to build the GAD models. In s801, a training data set of approved radiation therapy contours is accessed from the contour storage database by the processor 910. In s802, the geometric attribute calculation is performed. Three geometric attributes (centroid, volume, and shape) of each contour in the training data set can be calculated. In s803, an intra and interstructural GAD model is constructed. The interstructural GAD models are constructed to characterize the centroid and volume relationships between neighboring contours, and intrastructural GAD models are constructed to describe the slice-by-slice shape variations of individual contours.

Figure 11B:
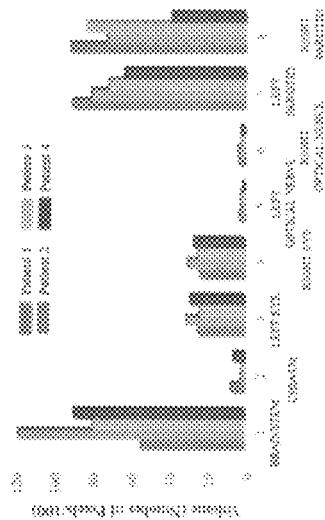
FIG. 11A-11C illustrates exemplary centroid and volume GAD models constructed from training data.
Figure 11C:
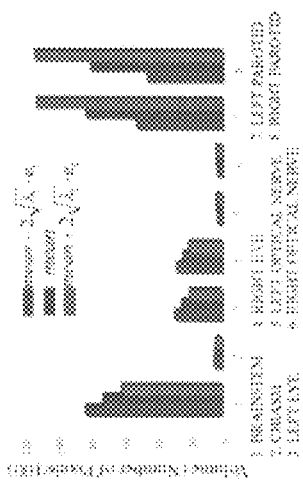
Figure 11A:
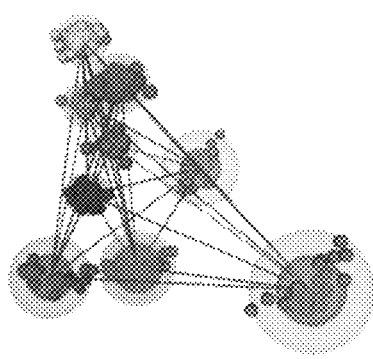

FIG. 11A shows exemplary aligned centroids constructed using an approved radiation therapy contour database. The centroid of each individual contour was shown in the smallest sphere, and corresponding mean centroid was displayed with the middle-size sphere. The largest sphere represents the maximum difference between each single centroid and the mean value. The constructed centroid GAD model can characterize the spatial relationship between the nine centroids. FIG. 11B shows example volume distribution within the GAD model from four sets of training data. FIG. 11C shows that by adjusting the weighting factors to −2, 0, and +2, the GAD model can be deformed to approximate the volume attribute in any new contour set.

In the error-testing stage, the radiation therapy contours for a given patient are retrieved in s804. From this patient specific radiation therapy contours, a geometric attribute is calculated in s805. From the intra- and interstructural GAD model of s803 and the geometric attribute of s805, a contouring error is detected through the iterative model fitting process in s806 and a contouring error report can be generated and stored. If the error detection yields a contouring attribute difference larger than a predefined, training-data-adaptive threshold, the tested contour can be denoted as incorrect for further verification.

In s807, the contouring error report is retrieved. In s808 a physician or other practitioners can use the contouring error report in order to verify the patient specific contours.

If the physician approves of the contouring in s808, radiation therapy can be planned and treatment using the patient specific contour performed in s809. Furthermore, the patient specific contour can be added to the approved radiation therapy contour database in s810 for the refinement of the GAD models. If the patient specific radiation therapy contour is approved, it can be used for radiation therapy planning and/or treatment in s811.

Figure 12A:
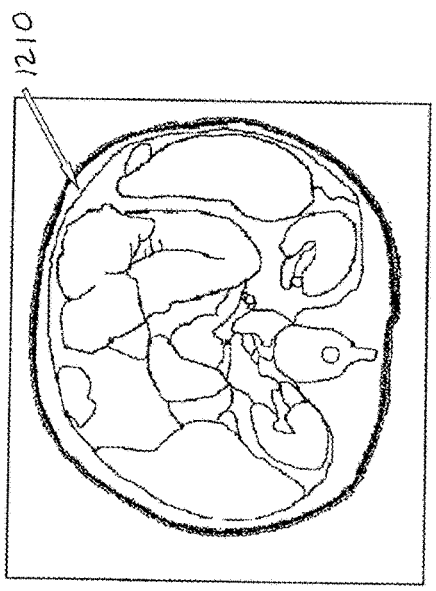
FIGS. 12A-12C illustrate an exemplary computerized representation undergoing analysis according to the present invention.
Figure 12B:
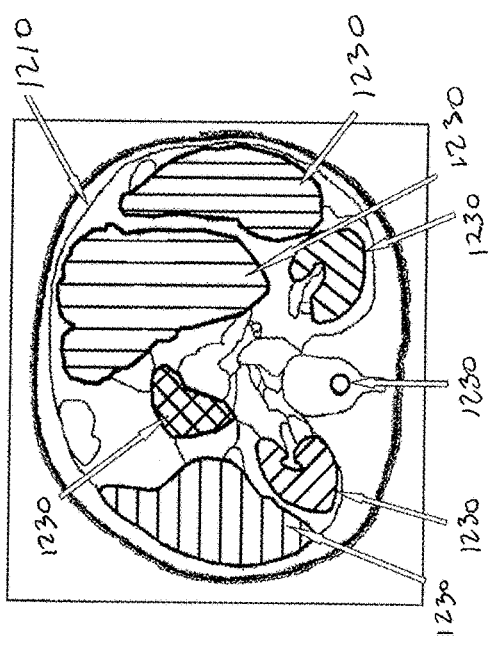
Figure 12C:
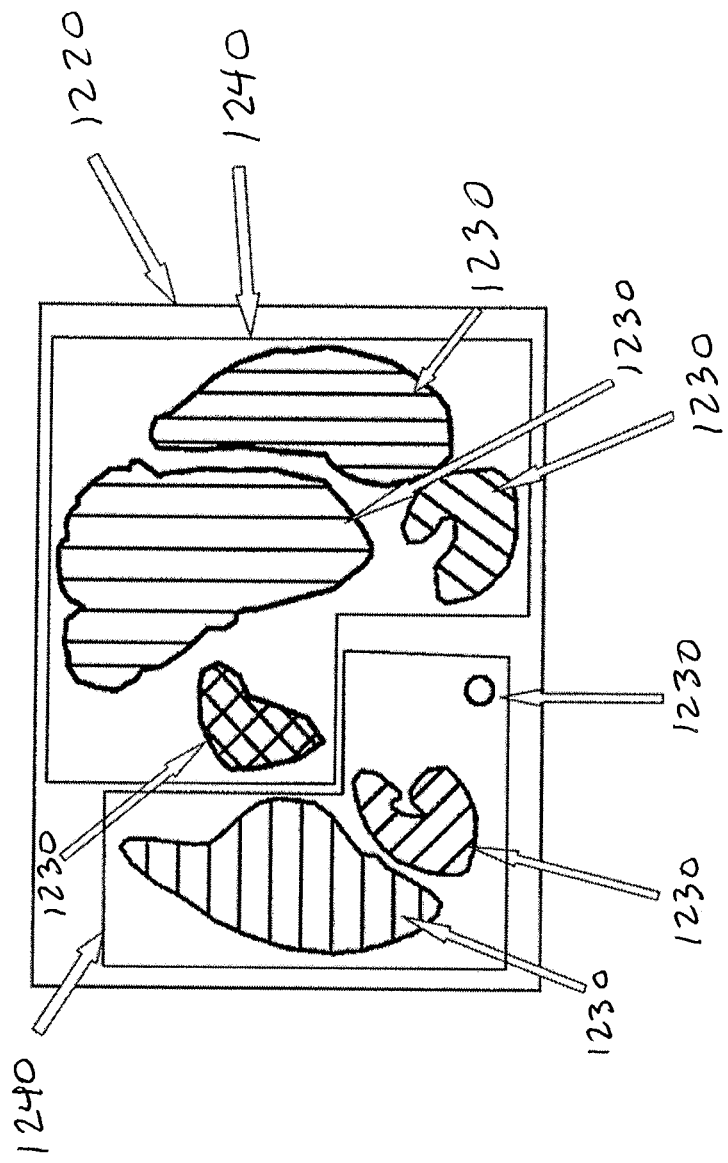

FIGS. 12A-12C show examples of computerized representations 1210 of a patient's anatomy, with delineated anatomical structures 1230 identified within delineated anatomical structure sets 1220. In FIG. 12C, there is shown an example as to how delineated anatomical structures 1230 might be grouped into two different delineated anatomical structure groupings 1240.

Although the example in FIGS. 12A-12C shows a computerized representation 1210 having a single delineated anatomical structure set 1220, it is noted that a computerized representation 10 may instead have two or more delineated anatomical structure sets 1220. Likewise, although the example in FIG. 12C shows a delineated anatomical structure set 1220 that has two groupings 1240, a computerized representation 1210 may have only one grouping 1240, or it may have three or more groupings 1240. Also, one or more groupings 1240 may overlap with one another by encompassing one or more common delineated anatomical structures 1230. Furthermore, although the examples in FIGS. 12B and 12C both show seven examples of delineated anatomical structures 30, the computerized representations 1210 may also have one to six, or eight or more delineated anatomical structures 30.

The interstructural GAD model of centroids is constructed based on training data sets to characterize the centroid relationships between neighboring contours and is employed to analyze a given patient case. The total number of training sets is M, and each training set includes N contours. The centroid of the nth contour in the $m^{th}$ training set is denoted as $g_{n,m}=(x,y,z)$, where $n=1,2, \ldots, N-1$, N as the index of contours; $m=1,2,\ldots, M-1$, M as the index of training sets. The centroid attributes are computed in 3D Euclidean space (i.e., in mm). The centroid attributes of the N contours in the $m^{th}$ training set are arranged as $G_m=[g_{1,m}, g_{2,m}, \ldots, g_{N-1,m}, g_{N,m}]$. Procrustes analysis is used to minimize the pose differences (isotropic scale, orientations, and positions) among the training contour sets for accurate centroid attribute distribution analysis. The mean geometric attribute is computed by $$\overline{G}_{cen} = \sum_{m=1}^{M} G_m / M.$$

The mean offset covariance matrix COV that describes the variance between each contour attribute $G_m$ and the corresponding mean $G_{cen}$ is calculated by $(G_m-\overline{G})^T {}^{(G}{}_m-\overline{G})$. Singular value decomposition (SVD) is used to decompose COV to obtain the corresponding eigenvalues $\lambda_i$, where $i=1, \ldots, S$, and S is the dimension of covariance matrix. Given the eigenvalues $\lambda_i$, which are arranged in decreasing order, one can determine a value of t, which is the minimum number satisfying $(G_m-\overline{G})^T {}^{(G}{}_m-\overline{G})$. Singular value decomposition (SVD) is used to decompose COV to obtain the corresponding eigenvalues $\lambda_i$, where $i=1, \ldots, S$, and S is the dimension of covariance matrix. Given the eigenvalues $\lambda_i$, which are arranged in decreasing order, one can determine a value of t, which is the minimum number satisfying $$\sum_{i=1}^{t} \left( \lambda_i \Big/ \sum_{j=1}^{S} \lambda_j \right) \geq 0.95.$$

Considering the t eigenvalues can preserve 95% of the total variance of the attributes. The t eigenvectors are represented by a matrix $E_{cen}=(e_1, e_2, \ldots, e_i, \ldots, e_{t-1}, e_t)$. By assigning a weighting factor to each component of $E_{cen}$, the combination of $G_{cen}$ and weighted $E_{cen}$ can represent a new centroid attribute as $G_{cen}=(g_1,g_2, \ldots, g_i, \ldots g_{N-1}, g_N)^{T\sim G}{}_{cen}+E_{cen}B_{cen}$, where $B_{cen}=(b_1,b_2,\ldots,b_i,\ldots,b_{t-1}b_t)^T$ represent the set of weighting factors.

In addition, following the same steps described above, the interstructural GAD model of volume, which is represented as $G_{vol}\approx G_{vol}+E_{vol}B_{vol}$, is created to characterize the volume relationships between neighboring contours. The volume attribute is computed in units of volume, such as cubic millimeters. Here, $G_{vol}$ represents the mean volume attribute of the M training sets, $E_{vol}$ denote the eigenvectors, and $B_{vol}$ are the weighting factors of $E_{vol}$. In the error-detecting stage, $G_{cen}$ or Gvol will be deformed to fit to the attribute of a given contour by adjusting either $B_{cen}$ or $B_{vol}$. The fitting difference will then be used to detect if the given contour has any errors due to incorrect centroid shifts or volume differences.

The interstructural GAD models described above characterize the positional and volumetric relationships between neighboring contours. The intrastructural GAD models of shapes are further proposed to detect contouring errors associated with incorrectly shaped contours, such as isolated points, missing slices, or unusually large/small slices. In order to construct a 3D surface point distribution model using conventional methods, a large number of corresponding landmarks should be selected from the training shapes. However, due to the lack of specific geometric properties and/or clear intensity characteristics, it is difficult to select a sufficient number of appropriate and consistent landmarks on some radiation therapy contours (e.g., brainstem in head-and-neck site). In order to overcome this issue, an implicit surface function is used, which can provide accurate continuous shape representation for landmark-less contours and high curvature boundaries, to construct the intrastructural shape GAD models.

To effectively compute the shape attribute of an individual contour from a radiation therapy 3D simulation image, which can be large, a local cuboid region that contains the contour is determined and utilized. The shape attribute of the nth contour of the mth training set can be represented by $\Psi_{n,m}$ $$\Psi_{n,m}(p_h) = \begin{cases} -dis(p_h) & \text{if } (p_h) \text{ belongs to the background} \\ 0 & \text{if } (p_h) \text{ is on the surface of the structure,} \\ dis(p_h) & \text{if } (p_h) \text{ belongs to the structure} \end{cases}$$

where $p_h$ represents the 3D coordinate of the hth voxel in the cuboid region of the nth contour; dis( ) is a signed-distance transform returning the shortest distance value of $p_h$ to the surface. The mean shape attribute of the nth contour for all M training sets is obtained by $\overline{\Psi}_n=\Sigma_{n=1}^{M}\Psi_{nm}/M$, with the m=1 aligned M structure surfaces. After applying the principal component analysis (PCA) to the mean-offset covariance matrix of the shape attribute, we can obtain the corresponding eigenvalues $U_n$. By assigning a weighting factor to each component of $U_n$, the combination of $\Psi_n$ and weighted $U_n$ can represent a new shape attribute, defined as $\Psi_n=(\Psi_n(p_1),\Psi_n(p_2), \ldots, \Psi_n(p_h), \ldots, \Psi_n(p_{H-1}), \Psi_n(p_H))^T \approx \Psi_n+U_n A_n$, where $A_n$ represent the weighting factors of $U_n$. H is the dimension of the shape attribute model determined by the number of voxels in the aligned local cuboid region that contains the nth contour. As with the interstructural GAD models, $\Psi_n$ will be deformed to fit to a given contour shape by adjusting $A_n$ in the error-detecting stage, and then the fitting difference will be used to detect the shape related contouring errors.

In the error detection stage, the centroid, volume, and shape contour attributes of a given contour set, denoted as $G_{cen}^e$, $G_{vol}^e$, $\Psi_n^e$ are first computed. The centroid and volume related contouring errors are detected by measuring the differences between the given contour's attribute distributions and those from the trained GAD models ($G_{cen}$, $G_{vol}$, and $\Psi_n$). Either the centroid or the volume difference E can be assessed by solving the following minimization problem:

$$\varepsilon = \min_{\Theta_k, B_k, W_k} \left\{ \frac{1}{N} \|W_k(G_k^e - T(\Theta_k))(\overline{G}_k + E_k B_k)\|_2 \right\}$$

where T is an affine transformation; $\Theta_k$ are the pose parameters (isotropic scaling factor, three-axes orientations, and translations factors) representing either the centroid attribute (k=cen) or the volume attribute (k=vol). $W_k$ is a diagonal matrix whose elements are binary values and are used to either include the related contouring attributes into the model-fitting process or exclude them from the model-fitting process. $G_k$ is deformed to fit to the attribute of a given contour by adjusting $B_k$. Specifically, $\Theta_k$ and $B_k$ are updated iteratively until the difference $\varepsilon$ is minimized. $\Theta_{k,(t+1)}$ in the (t+1)th iteration are estimated by using the Powell conjugate gradient method to minimize the following cost function $$\Theta_{k,t+1} = \operatorname*{argmin}_{\Theta_{k,t}} \left\{ \frac{1}{N} \|W_k(T^{-1}(\Theta_k)G_k^e - (\overline{G}_k + E_k B_k))\|_2 \right\}.$$

The residual $\Delta B$ is calculated as $\Delta B_{k,t+1}=E_k(T^{-1}(\Theta_k) G_k^e - (\overline{G}_k + E_k B_k))$. $B_k$ is normalized if they are over ±2 times the principal component variations (the square root of eigenvalues) of the attribute distributions in order to avoid generating over distorted distribution models.

FIG. 9 shows a schematic diagram of the iterative weighted inter structural GAD model-fitting procedure. The system parameters $T_1$ and $T_2$ are determined based on ROC analysis. The process begins at s901, where the parameters are initialized to a=0 and b=N. In s902, the model fitting is performed via minimizing the cost function $\Theta_{k,t+1}$. Based on the results of s902, the fitting difference is calculated in s903 and compared to $T_1$. If the fitting difference is less than or equal to $T_1$, the contour is marked as correct in s904, and the contour set is reported at correct in s905. If the fitting difference is greater than $T_1$, the process continues to s906. In s906, the model fitting process is repeated but with the nth contour excluded. In s907, the excluded contour yielding the smallest fitting difference $\varepsilon_a$ is denoted as having confirmed error. In s908, if $|\varepsilon_{a-1}-\varepsilon_a|$ is greater than $T_2$ or if b is equal to 1, the process continues to s905, and the contour status is reported. Otherwise, the process continues to s909, where a is incremented, and b is decremented.

The intrastructural shape model-fitting process is performed to detect incorrect slices in each individual anatomical contour by solving the following minimization problem:

$$\varepsilon = \min_{\Theta_n^*, A_n^*, W_k} \{\|\Psi_n^e - T(\Theta_n)\Psi_n\|_2\} \equiv \min_{\Theta_n^*, A_n^*, W_k} \{\|\Psi_n^e - T(\Theta_n)(\Psi_n + U_n A_n)\|_2\}$$

The nth contour shape is estimated as $\Psi_n \approx \Psi_n+U_n A_n$. The estimation of $\Theta_n$ and $A_n$ is similar to that of the estimation of $\Theta_k$ and $B_k$. Then, the closest distance for each point on the given surface with respect to the fitted GAD model surface is calculated, and the mean distance $E_{i,c}$ of all the surface points on the cth slice is obtained as $$E_{i,c} = \frac{1}{Q}\sum_{r=1}^{Q} \min\{\|v_r - v_s\|, s = 1, 2, \ldots, P-1, P\},$$

where $v_r$ represents the rth surface point of the total Q points on the cth slice of the given contour; $v_s$ is the sth surface point of the total P points on the fitted GAD model surface closest to $v_r$. If $E_{i,c}$ is smaller than a system-determined parameter $T_3$, the contour on the cth slice is considered as correct; otherwise, it is reported as incorrect. A k-dimensional tree, which is based on a binary partitioning process to handle the problem of nearest neighbor search with a complexity of O(log N), was implemented to speed up the multidimensional search process. As a single subject-dependent parameter, $T_3$ can be determined based on a box-and-whisker plot for each case.

Figure 13:
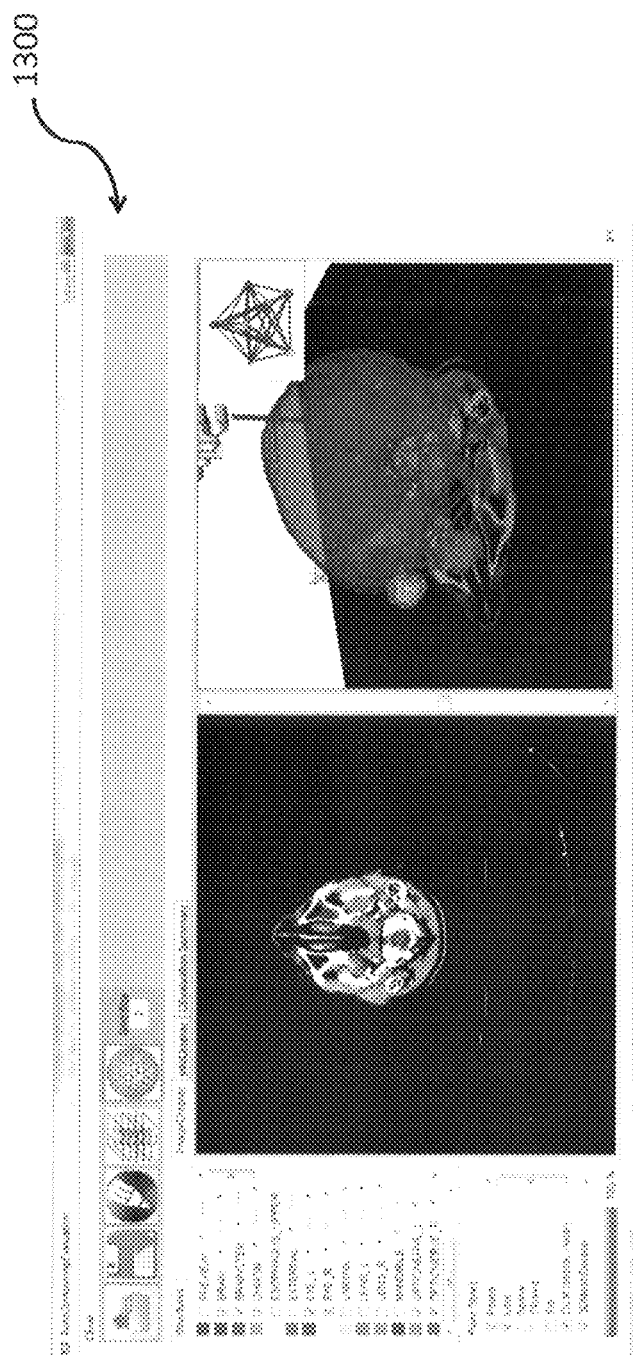
FIG. 13 illustrates a graphical user interface of the system.

The graphical user interface 1300 of the system 900 is shown in FIG. 13. The graphical user interface 1300 renders both the calculated contour attributes and the reference inter- and intrastructural GAD models. From the graphical user interface 1300, a user can upload the contours to the approved contours database. Users can also observe and evaluate the radiation therapy contours by superposing them onto the corresponding simulation image. When a patient specific contour is evaluated and has differences larger than $T_1$, $T_2$, or $T_3$, the system can report to the user than the error has exceed the thresholds and the evaluated contour was incorrect.

In addition, the graphical user interface 1300 provides additional functions to facilitate visual comparison. The software enables radiation therapy contour interpolation and surface triangulation to render surface models with adjustable opacity, as seen in the right of FIG. 13. The pretrained GAD models can also be loaded as a default and displayed for visual comparison with the given data, as seen in the upper right of FIG. 13 The software can automatically parse the DICOM header and list the header information in the "InfoDisplay" tablet for clinicians to view. The 3D visualization of the critical radiation therapy contours can be rotated 360° freely, with zoom-in and zoom-out accomplished by a simple manipulation of mouse click and drag, so that users can easily get a visual sense to verify the contouring errors that are reported in the "summary" tablet. The graphical user interface 1300 also allows clinicians to directly modify the reported incorrect radiation therapy contours by moving control points of radiation therapy contours (i.e., the small empty circles shown in the left of FIG. 13). The verified correct testing set can be added to the training set to update the trained GAD models and improve the stability of the contour quality evaluation strategy. The corrected radiation therapy contours can also be exported in a compatible format to other radiation therapy planning systems, so that it can be imported back to the clinical planning system if necessary.

Although the present invention has been described with reference to particular embodiments, it will be understood to those skilled in the art that the disclosure herein is exemplary only and that the invention may include additional features, including features that are known and used in the art; and that various other alternatives, adaptations, and modifications may be made within the scope and spirit of the present invention.

For example, a radiologist can first make an outline of the tumor (or other radiation target region) and all risk organs (or, more generally, risk regions). Then the system can automatically evaluate contouring results based on the machine learning process previously described. A treatment plan can also then be automatically generated and analyzed.

Additionally, the system can be configured to provide automated configuration based on the likely impact of reduced precision in the contouring. For example, during contouring of the prostate for prostate radiation therapy, the anatomical structures to be delineated typically include femur heads, the bladder, and the rectum. Certain contour segments require less accuracy of in terms of delineation, while other contour segments need to be quite accurate. The system can update the evaluation criteria based on the required accuracy for that structure.

Although the foregoing examples disclose the system 200 and system 900 outputting a quality assessment report to a user for manual evaluation and error correction, it will be appreciated by those skilled in the art that the system 200 or system 900 may further include an automated evaluation and correction process, with a user evaluation and correction being employed only when a subsequent automated judgment is made that the automated evaluation and correction process has failed to correct all recorded judgment errors.

Also, while the disclosed methods may be performed by executing all of the disclosed steps in the precise order disclosed, without any intermediate steps there between, those skilled in the art will appreciate that the methods may also be performed with further steps interposed between the disclosed steps; that the disclosed steps may be performed in orders other than those disclosed; and that one or more disclosed steps may be omitted.

In addition, although the foregoing examples disclose the system being initiated by a user through an input device (e.g., a graphical user interface), those skilled in the art will appreciate that the system may operate as a service program that executes the process in an automated fashion without a user request.

As such, the system can be integrated in a closed-loop manner with medical imaging devices and with radiation therapy devices. The system may receive images directly from the imaging device. The system may also execute process 800 with an operator in the loop to generate a manual contour that is evaluated in real-time, or the system may generate contours and evaluate the contours automatically. The system may also communicate directly with radiation therapy devices to create a radiation therapy plan based on the contours and other parameters.

To the extent necessary to understand or complete the disclosure of the present invention, all publications, patents, and patent applications mentioned herein are expressly incorporated by reference herein to the same extent as though each were individually so incorporated. In addition, ranges expressed in the disclosure are considered to include the endpoints of each range, all values in between the end points, and all intermediate ranges subsumed by the end points.

Accordingly, the present invention is not limited to the specific embodiments as illustrated herein, but is instead characterized by the appended claims.

What is claimed is:

1. A system for validating accuracy of delineated contours in computerized imaging, comprising:
   a storage unit including one or more approved radiation therapy contours and a patient specific radiation therapy contour; and
   a processor programmed to:
   receive the one or more approved radiation therapy contours,
   calculate a geometric attribute of the one or more approved radiation therapy contours,
   construct assessment criterion parameters using machine learning methods,
   receive the patient specific radiation therapy contour from the storage unit,
   calculate a patient specific radiation therapy contour geometric attribute using the patient specific radiation therapy contour, and
   detect contouring error by fitting the geometric attribute of the patient specific radiation therapy contour to the assessment criterion parameters.

2. The system of claim 1, wherein the processor is further programmed to update the assessment criterion parameters using the one or more approved radiation therapy contours.

3. The system of claim 1, further comprising a graphical display unit programmed to at least one of visualize the contouring error by using a software graphical user interface and using graphics techniques to present one or more differences between the patient specific radiation therapy contour and the assessment criterion parameters.

4. The system of claim 3, wherein the graphical display unit is further programmed to allow clinicians to directly modify one or more reported incorrect radiation therapy contours by moving control points of the one or more reported incorrect radiation therapy contours.

5. The system of claim 1, wherein the patient specific radiation therapy contour corresponds to a patient receiving adaptive radiation therapy.

6. The system of claim 1, wherein the patient specific radiation therapy contour corresponds to a patient receiving on-line adaptive radiation therapy.

7. The system of claim 1, wherein the processor is further programmed to add, in the storage unit, the patient specific radiation therapy contour to the one or more approved radiation therapy contours.

8. The system of claim 1, wherein the processor is further programmed to generate an error report based on the contouring error.

9. The system of claim 8, wherein the processor is further programmed to transmit the error report over a computer network.

10. A system for validating accuracy of delineated contours in computerized imaging, comprising:
    a storage unit including one or more approved radiation therapy contours and a patient specific radiation therapy contour; and
    a processor programmed to:
    receive the one or more approved radiation therapy contours, calculate at least one attribute of the one or more approved radiation therapy contours,
construct assessment criterion parameters using machine learning,
receive the patient specific radiation therapy contour from the storage unit,
calculate at least one patient specific radiation therapy contour attribute using the patient specific radiation therapy contour, and
detect contouring error by fitting the at least one patient specific radiation therapy contour to the assessment criterion parameters.

* * * * *